United States Patent

Stengel

(10) Patent No.: US 10,490,754 B2
(45) Date of Patent: Nov. 26, 2019

(54) TRANSITION METAL COMPLEXES WITH TRIPODAL LIGANDS AND THE USE THEREOF IN OLEDS

(71) Applicant: UDC IRELAND LIMITED, Dublin (IE)

(72) Inventor: Ilona Stengel, Dublin (IE)

(73) Assignee: UDC IRELAND LIMITED, Dublin (IE)

( * ) Notice: Subject to any disclaimer, the term of this patent is extended or adjusted under 35 U.S.C. 154(b) by 375 days.

(21) Appl. No.: 15/388,371

(22) Filed: Dec. 22, 2016

(65) Prior Publication Data

US 2017/0194576 A1    Jul. 6, 2017

(30) Foreign Application Priority Data

Dec. 21, 2015 (EP) .................................... 15201529

(51) Int. Cl.
*C07F 15/00* (2006.01)
*H01L 51/00* (2006.01)
(Continued)

(52) U.S. Cl.
CPC ...... *H01L 51/0085* (2013.01); *C07F 15/0033* (2013.01); *C09K 11/025* (2013.01);
(Continued)

(58) Field of Classification Search
None
See application file for complete search history.

(56) References Cited

U.S. PATENT DOCUMENTS 6,358,631 B1 * 3/2002 Forrest .................. C09K 11/06
257/E33.056
8,154,194 B2 * 4/2012 Male ..................... C07F 13/005
313/504
(Continued)

FOREIGN PATENT DOCUMENTS

DE    102010004453    7/2011
EP    1713136    10/2006
(Continued)

OTHER PUBLICATIONS

Szczepura et al. "Tris(2-pyridyl) tripod ligands" Coordination Chemistry Reviews, 1998, 174, 5-32. (Year: 1988).*
(Continued)

*Primary Examiner* — Robert S Loewe
(74) *Attorney, Agent, or Firm* — Riverside Law LLP

(57) ABSTRACT

The present invention relates to metal complexes of the general formula $L^1ML^2$ (I), wherein
M is selected from Ir and Rh,
$L^1$ is a ligand of formula (Continued)

Figure 1:
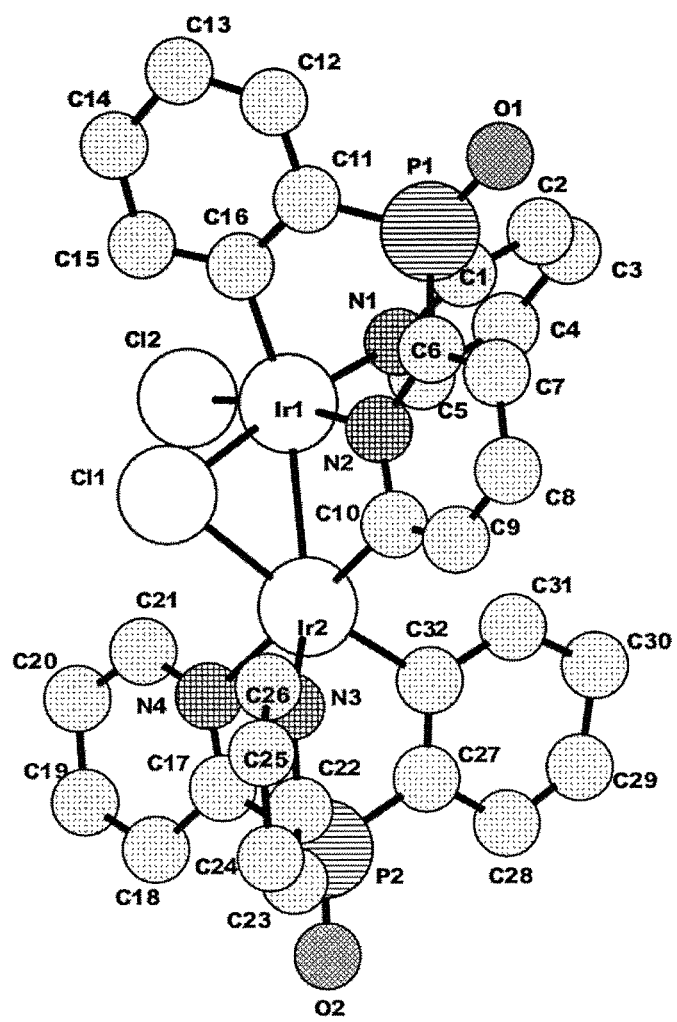

$L^2$ is a ligand of formula (IIb)

to OLEDs (Organic Light-Emitting Diodes) which comprise such complexes, to a device selected from the group consisting of illuminating elements, stationary visual display units and mobile visual display units comprising such an OLED, to the use of such a metal complex in OLEDs, for example as emitter, matrix material, charge transport material and/or charge or exciton blocker.

20 Claims, 2 Drawing Sheets

(51) Int. Cl.
C09K 11/02 (2006.01)
C09K 11/06 (2006.01)
H01L 51/05 (2006.01)
H01L 51/42 (2006.01)
H01L 51/50 (2006.01)

(52) U.S. Cl.
CPC ...... C09K 11/06 (2013.01); C09K 2211/1007 (2013.01); C09K 2211/1014 (2013.01); C09K 2211/1029 (2013.01); C09K 2211/185 (2013.01); H01L 51/05 (2013.01); H01L 51/42 (2013.01); H01L 51/5016 (2013.01); Y02E 10/549 (2013.01)

(56) References Cited

U.S. PATENT DOCUMENTS

| | | | |
|---|---|---|---|
| 2003/0059647 A1* | 3/2003 | Thompson | C09K 11/06 428/690 |
| 2005/0170206 A1* | 8/2005 | Ma | C07F 5/069 428/690 |
| 2006/0073360 A1* | 4/2006 | Ise | C07F 15/0033 428/690 |
| 2006/0182992 A1* | 8/2006 | Nii | C07C 251/24 428/690 |
| 2006/0188745 A1 | 8/2006 | Liao | |
| 2006/0240280 A1 | 10/2006 | Liao | |
| 2006/0263633 A1* | 11/2006 | Ichijima | C09K 11/06 428/690 |
| 2007/0092755 A1 | 4/2007 | Begley | |
| 2007/0278938 A1 | 12/2007 | Yabunouchi | |
| 2008/0014464 A1 | 1/2008 | Kawamura | |
| 2008/0106190 A1 | 5/2008 | Yabunouchi | |
| 2008/0241589 A1* | 10/2008 | Fukunaga | C07F 9/5027 428/690 |
| 2008/0265216 A1 | 10/2008 | Hartmann | |
| 2009/0283757 A1 | 11/2009 | Seo | |
| 2009/0322217 A1 | 12/2009 | Inoue | |
| 2010/0001638 A1 | 1/2010 | Kawakami | |
| 2010/0044689 A1 | 2/2010 | Nishimura | |
| 2010/0060154 A1 | 3/2010 | Nomura | |
| 2010/0060155 A1 | 3/2010 | Seo | |
| 2010/0076201 A1 | 3/2010 | Suzuki | |
| 2010/0096981 A1 | 4/2010 | Seo | |
| 2010/0102709 A1 | 4/2010 | Zeika | |
| 2010/0156957 A1 | 6/2010 | Ogita | |
| 2010/0219400 A1 | 9/2010 | Arakane | |
| 2010/0244004 A1 | 9/2010 | Xia | |
| 2011/0006670 A1 | 1/2011 | Katakura | |
| 2011/0022749 A1 | 1/2011 | Kobayashi | |
| 2011/0147792 A1 | 6/2011 | Kawata | |
| 2011/0163302 A1 | 7/2011 | Lin | |
| 2011/0177641 A1 | 7/2011 | Cheon | |
| 2011/0186825 A1 | 8/2011 | Egawa | |
| 2011/0198574 A1 | 8/2011 | Egawa | |
| 2011/0210316 A1 | 9/2011 | Kadoma | |
| 2011/0215714 A1 | 9/2011 | Seo | |
| 2011/0279020 A1 | 11/2011 | Inoue | |
| 2011/0284835 A1 | 11/2011 | Osaka | |
| 2011/0285276 A1 | 11/2011 | Kadoma | |
| 2012/0025697 A1 | 2/2012 | Kadoma | |
| 2012/0061651 A1 | 3/2012 | Osaka | |
| 2012/0104369 A1 | 5/2012 | Kawata | |
| 2012/0104422 A1 | 5/2012 | Lee | |
| 2012/0130081 A1 | 5/2012 | Kawata | |
| 2012/0132896 A1 | 5/2012 | Kawata | |
| 2012/0133274 A1 | 5/2012 | Kawakami | |
| 2012/0223296 A1 | 9/2012 | Werner | |
| 2012/0235123 A1 | 9/2012 | Lee | |
| 2012/0261654 A1 | 10/2012 | Yasukawa | |
| 2012/0305901 A1 | 12/2012 | Kim | |
| 2013/0119354 A1 | 5/2013 | Ma | |
| 2013/0181190 A1 | 7/2013 | Ma | |
| 2014/0001446 A1 | 1/2014 | Mizuki | |
| 2014/0027716 A1* | 1/2014 | Tsai | C07F 15/0033 257/40 |
| 2014/0217392 A1 | 8/2014 | Hong | |
| 2015/0073142 A1 | 3/2015 | Ohsawa | |
| 2015/0102331 A1 | 4/2015 | Seo | |
| 2015/0194615 A1* | 7/2015 | Lin | C07F 15/0093 257/40 |

FOREIGN PATENT DOCUMENTS

| | | |
|---|---|---|
| EP | 1786050 | 5/2007 |
| EP | 1837926 | 9/2007 |
| EP | 1837927 | 9/2007 |
| EP | 1988587 | 11/2008 |
| EP | 2180029 | 4/2010 |
| EP | 2246862 | 11/2010 |
| EP | 2363398 | 9/2011 |
| EP | 2401254 | 1/2012 |
| EP | 2434559 | 3/2012 |
| EP | 2452946 | 5/2012 |
| EP | 13191100 | 10/2013 |
| JP | 2008127326 | 6/2008 |
| JP | 2013095688 | 5/2013 |
| WO | 2005019373 | 3/2005 |
| WO | 2006056418 | 6/2006 |
| WO | 2007031773 | 3/2007 |
| WO | 2007071450 | 6/2007 |
| WO | 2007115970 | 10/2007 |
| WO | 2007115981 | 10/2007 |
| WO | 2008000727 | 1/2008 |
| WO | 2008031743 | 3/2008 |
| WO | 2008065975 | 6/2008 |
| WO | 2009021126 | 2/2009 |
| WO | 2010002850 | 1/2010 |
| WO | 2010028151 | 3/2010 |
| WO | 2010047707 | 4/2010 |
| WO | 2010056669 | 5/2010 |
| WO | 2010079051 | 7/2010 |
| WO | 2010132236 | 11/2010 |
| WO | 2010145991 | 12/2010 |
| WO | 2011109042 | 9/2011 |
| WO | 2011136755 | 11/2011 |
| WO | 2011143563 | 11/2011 |
| WO | 2011157779 | 12/2011 |
| WO | 2011157790 | 12/2011 |
| WO | 2012004765 | 1/2012 |
| WO | 2012014621 | 2/2012 |
| WO | 2012016601 | 2/2012 |
| WO | 2012023947 | 2/2012 |
| WO | 2012045710 | 4/2012 |
| WO | 2012108879 | 8/2012 |

(56) References Cited

FOREIGN PATENT DOCUMENTS

| WO | 2012108881 | 8/2012 |
|---|---|---|
| WO | 2012111462 | 8/2012 |
| WO | 2012115034 | 8/2012 |
| WO | 2012121936 | 9/2012 |
| WO | 2012130709 | 10/2012 |
| WO | 2012147397 | 11/2012 |
| WO | 2012172482 | 12/2012 |
| WO | 2013022419 | 2/2013 |
| WO | 2013050401 | 4/2013 |
| WO | 2013079678 | 6/2013 |
| WO | 2013112557 | 8/2013 |
| WO | 2013187896 | 12/2013 |
| WO | 2014009317 | 1/2014 |
| WO | 2014044722 | 3/2014 |
| WO | 2015014791 | 2/2015 |

OTHER PUBLICATIONS

Maleckis et al. "Facial Tridentate Ligands for Stabilizing Palladium(IV) Complexes" Organometallics 2011, 30, 6617-6627. (Year: 2011).*

Heinekey et al. "Cyclonnetalation of a Pyrazolyl Arm in Hydridotris(1-pyrazolyl)borate and Tris(1-pyrazolyl)methane Complexes of Iridium" J. Am. Chem. Soc. 1996, 118, 12842-12843. (Year: 1996).*

McWhinnie et al. "Complexes of Tri-(2-pyridyl)amine. Part I. Complexes with Cobalt(II), Nickel(II), and Copper(II) Perchlorated" J. Chem. Soc. A 1966, 1199-1203. (Year: 1966).*

Trofimenko, S.; "Recent advances in poly(pyrazolyl)borate (scorpionate) chemistry", Chem. Rev., 1993, 93:943-980.

Takeuchi, Kenneth J.; "Tris(2-pyridyl)tripod ligands", Coordination Chemistry Reviews, 1998, 174:5-32.

Heinekey, D. M. et al., "Cyclometalation of a Pyrazolyl Arm in Hydridotris(1-pyrazolyl)borate and Tris(1-pyrazolyl)methane Complexes of Iridium", J. Am. Chem. Soc. 1996, 118:12842-12843.

Sanford, Melanie S. et al., "Facial Tridentate Ligands for Stabilizing Palladium(IV) Complexes", Organometallics 2011, 30:6617-6627.

Casares, J. A.; "Kinetic Study of the Dynamic Behavior of [M(C6F5)X(OPPynPh3-n)] (M=Pd, Pt; X=C6F5, Halide; n=1-3): Activation Parameters for the Restricted Rotation about the M-Aryl Bond and for the Py Associative Exchange", Organometallics 1997, 16:770-779.

Wiley, Jackson S. et al., "Carbon-Hydrogen Bond Activation in Hydridotris(pyrazolyl)borate Complexes of Iridium", Organometallics 2000, 19:1670-1676.

Minghetti, Giovanni et al., "Reactivity of Ph2P(O)py-2 with Platinum(II) Alkyl Derivatives—Building-up of a Chiral Phosphorus Atom through C,N-Cyclometallation", Eur. J. Inorg. Chem. 2002, 431-438.

Casares, Juan S. et al., "Rhodium(I) Complexes with OPPy2Ph and OPPy3 (Py=2-Pyridyl), and Their Behavior in Hydrogenation Reactions", Eur. J. Inorg. Chem. 2001, 289-296.

Trofimenko, S., "Boron-Pyrazole Chemistry", J. Am. Chem. Soc. 1966, 88:1842-1844.

Gneuß, Timo et al., "A new class of luminescent Cu(I) complexes with tripodal ligands—TADF emitters for the yellow to red color range", Dalton Trans. 2015, 44:8506-8520.

Garcia-Rodríguez, Raúl et al., "Synthesis and structures of tris(2-pyridyl)aluminate sandwich compounds [{RAI(2-py')2}2M] (py'= 2-pyridyl, M=Ca, Mn, Fe)", Dalton Trans. 2014, 43:14045-14053.

Chen, Tsun-Ren et al., "An 18+δ iridium dimer releasing metal-loradicals spontaneously", Dalton Trans. 2010, 39:9458-9461.

Keene, Richard F. et al., "Ruthenium(II) complexes of the C3v ligands tris(2-pyridyl)amine, tris(2-pyridyl)methane, and tris(2-pyridyl)phosphine. 1. Synthesis and x-ray structural studies of the bis(ligand) complexes", Inorg. Chem. 1988 27:2040-2045.

Li, Organic Light-Emitting Materials and Devices, CRC Press, Taylor & Francis, 2015.

Khavasi, Hamid Reza et al., "Discrete Cubane-like Bromide-Water Cluster", Cryst. Growth Des. 2011, 11:933-935.

Gustafsson, G. et al., "Flexible light-emitting diodes made from soluble conducting polymers", Nature, 1992, 357:477-479.

Hu, Nan-Xing et al., "Novel high Tg hole-transport molecules based on indolo[3,2-b]carbazoles for organic light-emitting devices", Synth. Met., 2000, 111:421-424.

Gao et al., "Controlled p doping of the hole-transport molecular material N,N'-diphenyl-N,N'-bis(1-naphthyl)-1,1'-biphenyl-4,4'-diamine with tetrafluorotetracyanoquinodimethane", J. Appl. Phys., 2003, 94:359-366.

Werner et al., "Pyronin B as a donor for n-type doping of organic thin films", Appl. Phys. Lett., 2003, 82:4495-4497.

Pfeiffer et al., "Doped organic semiconductors: Physics and application in light emitting diodes", Organic Electronics, 2003, 4:89-103.

Walzer et al., "Highly Efficient Organic Devices Based on Electrically Doped Transport Layers", Chem. Soc. Rev., 2007, 107:1233-1271.

Kahn, "Use of a High Electron-Affinity Molybdenum Dithiolene Complex to p-Dope Hole-Transport Layers", J. Am. Chem. Soc., 2009, 131:12530-12531.

Kido et al., "2-Phenylpyrimidine skeleton-based electron-transport materials for extremely efficient green organic light-emitting devices", Chem. Commun., 2008, 5821-5823.

Kido et al., "Wide-Energy-Gap Electron-Transport Materials Containing 3,5-Dipyridylphenyl Moieties for an Ultra High Efficiency Blue Organic Light-Emitting Device", Chem. Mater., 2008, 20:5951-5953.

* cited by examiner

TRANSITION METAL COMPLEXES WITH TRIPODAL LIGANDS AND THE USE THEREOF IN OLEDS

CROSS-REFERENCE TO RELATED APPLICATIONS

The present application claims priority to European Patent Application No. 15201529.3, filed on Dec. 21, 2015, which is incorporated by reference herein in its entirety.

DESCRIPTION

The present invention relates to metal complexes with cyclometalated tripodal ligands, to OLEDs (Organic Light-Emitting Diodes) which comprise such complexes, to a device selected from the group consisting of illuminating elements, stationary visual display units and mobile visual display units comprising such an OLED, to the use of such a metal complex in OLEDs, for example as emitter, matrix material, charge transport material and/or charge or exciton blocker.

Organic light-emitting diodes (OLEDs) exploit the propensity of materials to emit light when they are excited by electrical current. OLEDs are of particular interest as an alternative to cathode ray tubes and liquid-crystal displays for production of flat visual display units. Owing to the very compact design and the intrinsically low power consumption, devices comprising OLEDs are suitable especially for mobile applications, for example for applications in cellphones, smartphones, digital cameras, mp3 players, laptops, etc. In addition, white OLEDs give great advantages over the illumination technologies known to date, especially a particularly high efficiency.

Tripodal ligands are well known in organometallic chemistry. The most common class of tripodal ligands are tris(pyrazolyl)borates (Chem. Rev. 1993, 93, 943-980). Also tripodal polypyridyl compounds are well known as ligands for metal complexes (Coord. Chem. Rev. 1998, 174, 5-32). In general, these ligands are N-chelates. There are very few compounds described in which a tripodal (or potentially tripodal) ligand coordinates to the metal cation via a cyclometalated C atom (JACS 1996, 118, 12842-12843, Organometallics 2011, 30, 6617-6627, Eur. J. Inorg. Chem. 2002, 431-438, Organometallics 2000, 19, 1670-1676).

Scorpionate (tris(pyrazolyl)borate) complexes exist with a huge variety of different metal centers, also iridium. They were discovered by Swiatoslaw Trofimenko in 1966 at du Pont (JACS 1966, 88, 1842-1844). Most of these Ir(III) complexes bear one tripodal ligand and other ligands in addition (Scorpionates: The Coordination Chemistry of Polypyrazolylborate Ligands, Swiatoslaw Trofimenko, 1999, World Scientific Pub Co Inc).

Cu(I) complexes with tripodal ligands have been synthesized and used as thermally assisted delayed fluorescence (TADF) emitters (Dalton Trans. 2015, 44, 8506). These tetrahedral Cu(I) complexes bear one tris(2-pyridyl) ligand and iodide in the fourth coordination position. They show emission colours from yellow to red.

WO2007031773A1 discloses transition metal complexes (Ir, Re, a.o.) with one tripodal ligand (scorpionates and trispyridyl compounds) as emitters in OLEDs.

There are also complexes described with two tris(2-pyridyl) ligands, which capture the metal cation in a sandwich like structure,

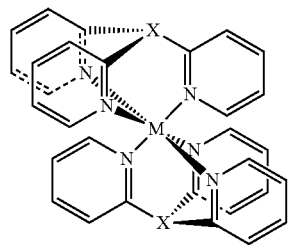

($M=Ru^{2+}$, X=N, CH, P, Inorg. Chem. 1988, 27, 2040-2045; $M=Ca^{2+}$, $Mn^{2+}$, or $Fe^{2+}$, X=[(Alkyl)Al]—, Dalton Trans. 2014, 43, 14045-14053, $M=Fe^{2+}$, X=P=O, Cryst. Growth Des. 2011, 11, 933-935).

US2006/0263633A1 reports Ir(III) complexes with two cyclometalated tripodal ligands as emitter materials for OLEDs. Among others the following metal complex

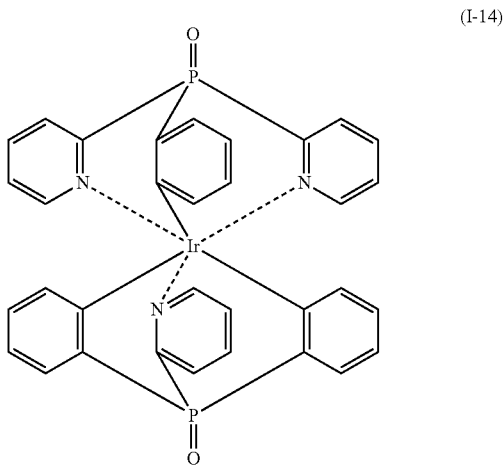

(I-14)

is mentioned. US2006/0263633A1 describes no process for the the production of the Ir(III) complexes described therein and discloses no physical data for the Ir(III) complexes described therein.

Besides the paper examples of US2006/0263633A1 no metal complex with a cyclometalated tripodal ligand in a three-fold coordination mode is known in literature, only either without cyclometalation or with cyclometalation but in a bidentate coordination mode. There are published papers and patents about metal complexes with cyclometalated ligands which could act as a three-fold coordinated tripodal ligand, but are actually only two-fold coordinated (Organomet. 1997, 16, 770-779, Eur. J. Inorg. Chem. 2001, 289-296, Eur. J. Inorg. Chem. 2002, 431-438, JP2013095688A).

Furthermore, US20140027716A1 describes the synthesis of several iridium complexes with three bidentate ligands, in which some of the ligands are potential tripodal ligands. It is shown that by applying conventional and literature known reaction conditions, starting materials and reagents, it is not possible to obtain a three-fold coordination of the cyclometalated potential tripodal ligand, at least not without a specific and newly established synthesis.

Additionally, Applicant found, that if a cyclometalated Ir(III) complex, e.g. (bis(2-pyridyl)phenylphosphine oxide) iridium dichloride, is heated in ethylene glycol at 195° C. without Ag-reagents,

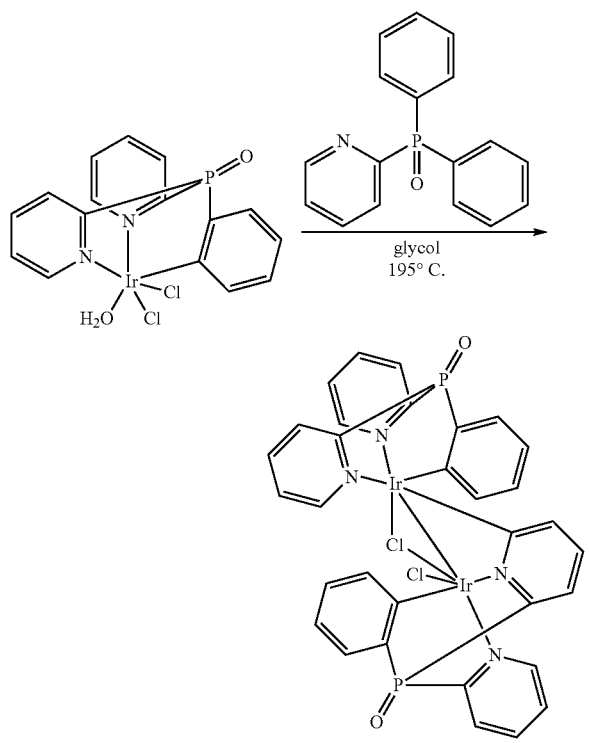

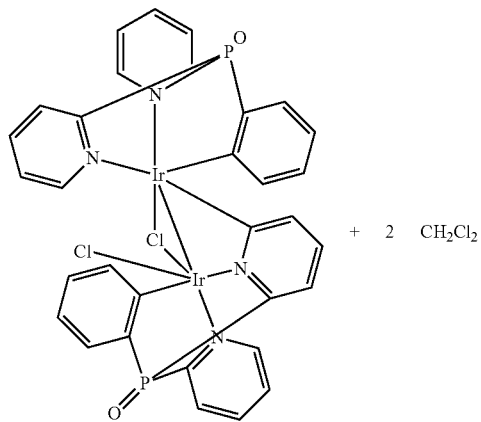

either with or without an additional trisarylphosphine oxide ligand, a dimeric product is obtained as the main product. According to the proton NMR spectrum and HPLC-MS the product was isolated as a mixture of three different isomers. The compound is not luminescent, neither in solution nor in the solid state. Single crystals of one isomer could be obtained after slow evaporation of the solvent from a concentrated dichloromethane solution. The result of the X-ray structure analysis of is shown in FIG. 1.

The product is a binuclear Ir(III) complex. Each Ir(III) center has one cyclometalated tripodal bis(2-pyridyl)phenylphosphine oxide ligand. One pyridine moiety works as a bridging ligand by being coordinated to one Ir(III) via N and to the other Ir(III) by the cylometalated ortho C atom. Additionally, two chloride ligands are present, one of them as a bent bridge. Thus, there is the possibility of an Ir—Ir bond between the two metal cores. A similar observation was published in 2010 for Ir(III) cores carrying two electrondeficient bidentate ligands each, and forming a 18+δ dimer (Dalton Trans. 2010, 39, 9458-9461).

Even though there are already known Ir complexes which are suitable for use in OLEDs, especially as light-emitting substances, it is desirable to provide more stable and/or more efficient compounds which are usable in industry.

It is therefore an object of the present invention to provide metal complexes which are suitable for use in organic electronic devices. More particularly, the metal complexes shall be suitable for use in OLEDs as emitters, matrix material, charge transport material, and/or charge blockers. The complexes shall be particularly suitable for color-tuning of the electroluminescence, which enables, for example, the production of full-color displays and white OLEDs. It is a further object of the present invention to provide corresponding complexes which can be used as a mixture with a host compound (matrix material) or as a pure layer as a light-emitting layer in OLEDs. More particularly, it is desirable to provide Ir and Rh transition metal complexes which exhibit a spectrum of properties improved over known Ir and Rh complexes, for example improved efficiencies, improved CIE color coordinates, suitable emission shape to enable the fabrication of white OLEDs with high CRI and/or improved lifetime/stability.

Surprisingly, it was found that these objects are achieved in accordance with the invention by metal complexes of formula $L^1ML^2$ (I), wherein M is selected from Ir and Rh, $L^1$ is a ligand of formula

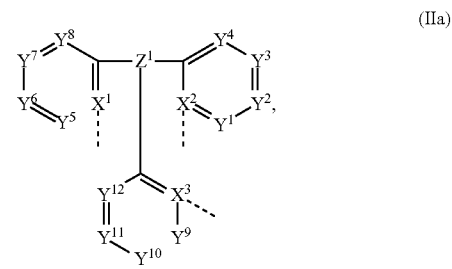

(IIa)

$L^2$ is a ligand of formula

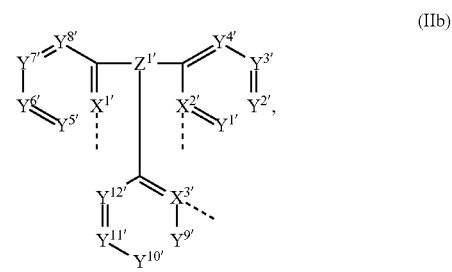

(IIb)

wherein $Z^1$ and $Z^{1'}$ are independently of each other N, P, P═O, P═S, As, Sb, Bi, B—$R^1$, Al—$R^2$, C—$R^3$, Si—$R^4$, or GeR$^5$, $X^1$, $X^2$, $X^3$, $X^{1'}$, $X^{2'}$ and $X^{3'}$ are independently of each other N, or C, $R^1$, $R^2$, $R^3$, $R^4$ and $R^5$ are independently of each other a $C_1$-$C_{18}$alkyl group, which can optionally be substituted by at least one substituent E and/or interrupted by D; a $C_6$-$C_{14}$aryl group, which can optionally be substituted by at least one substituent G; a heteroaryl group comprising 3 to 11 ring atoms, which can optionally be substituted by at least one substituent G, a $C_3$-$C_{12}$cycloalkyl group, which can optionally be substituted by at least one substituent E; or a $C_1$-$C_{18}$alkoxy group, $Y^1$, $Y^2$, $Y^3$, $Y^4$, $Y^5$, $Y^6$, $Y^7$, $Y^8$, $Y^9$, $Y^{10}$, $Y^{11}$, $Y^{12}$, $Y^{1'}$, $Y^{2'}$, $Y^{3'}$, $Y^{4'}$, $Y^{5'}$, $Y^{6'}$, $Y^{7'}$, $Y^{8'}$, $Y^{9'}$, $Y^{10'}$, $Y^{11'}$ and $Y^{12'}$ are independently of each other $CR^6$, or N, $R^6$ is independently in each occurence H, a halogen atom, especially F or Cl; $NO_2$; a $C_1$-$C_{18}$haloalkyl group such as $CF_3$; CN; $C_1$-$C_{18}$alkyl group, which can optionally be substituted by at least one substituent E and/or interrupted by D; a $C_6$-$C_{14}$aryl group, which can optionally be substituted by at least one substituent G; a heteroaryl group comprising 3 to 11 ring atoms, which can optionally be substituted by at least one substituent G; a —O—$C_6$-$C_{14}$aryl group, which can optionally be substituted by at least one substituent G; a $C_3$-$C_{12}$cycloalkyl group, which can optionally be substituted by at least one substituent E; or a $C_1$-$C_{18}$alkoxy group, $NR^7R^8$ or $SiR^{80}R^{81}R^{82}$;

$R^7$ and $R^8$ are independently of each other H, an unsubstituted $C_6$-$C_{18}$aryl group; a $C_6$-$C_{18}$aryl group which is substituted by $C_1$-$C_{18}$alkyl, $C_1$-$C_{18}$alkoxy; or a $C_1$-$C_{18}$alkyl group, which can optionally be interrupted by —O—;

D is —S—, $NR^{65}$, or —O—

E is —$OR^{69}$, $CF_3$, $C_1$-$C_8$alkyl or F;

G is —$OR^{69}$, $CF_3$ or $C_1$-$C_8$alkyl;

$R^{65}$ is a phenyl group, which can optionally be substituted by one or two $C_1$-$C_8$alkyl groups; an unsubstituted $C_1$-$C_{18}$alkyl group; or a $C_1$-$C_{18}$alkyl group, which is interrupted by —O—;

$R^{69}$ is a phenyl group, which can optionally be substituted by one or two $C_1$-$C_8$alkyl groups; an unsubstituted $C_1$-$C_{18}$alkyl group; or a $C_1$-$C_{18}$alkyl group, which is interrupted by —O—, $R^{80}$, $R^{81}$ and $R^{82}$ are independently of each other a $C_1$-$C_{25}$alkyl group, which can optionally be interrupted by O; a $C_6$-$C_{14}$aryl group, which can optionally be substituted by $C_1$-$C_{18}$alkyl; or a heteroaryl group comprising 3 to 11 ring atoms, which can optionally be substituted by $C_1$-$C_{18}$alkyl, and $\cdot^{\prime}$ is the bonding site to M, with the proviso that three of $X^1$, $X^2$, $X^3$, $X^{1'}$, $X^{2'}$ and $X^{3'}$ are C.

The present invention also relates to an organic electronic device, preferably an organic light-emitting diode (OLED), organic photovoltaic cell (OPV), organic field-effect transistor (OFET) or light-emitting electrochemical cell (LEEC), comprising at least one inventive metal complex with cyclometalated tripodal ligands.

In addition, the present invention also relates to a light-emitting layer comprising at least one inventive metal complex.

Figure 2:
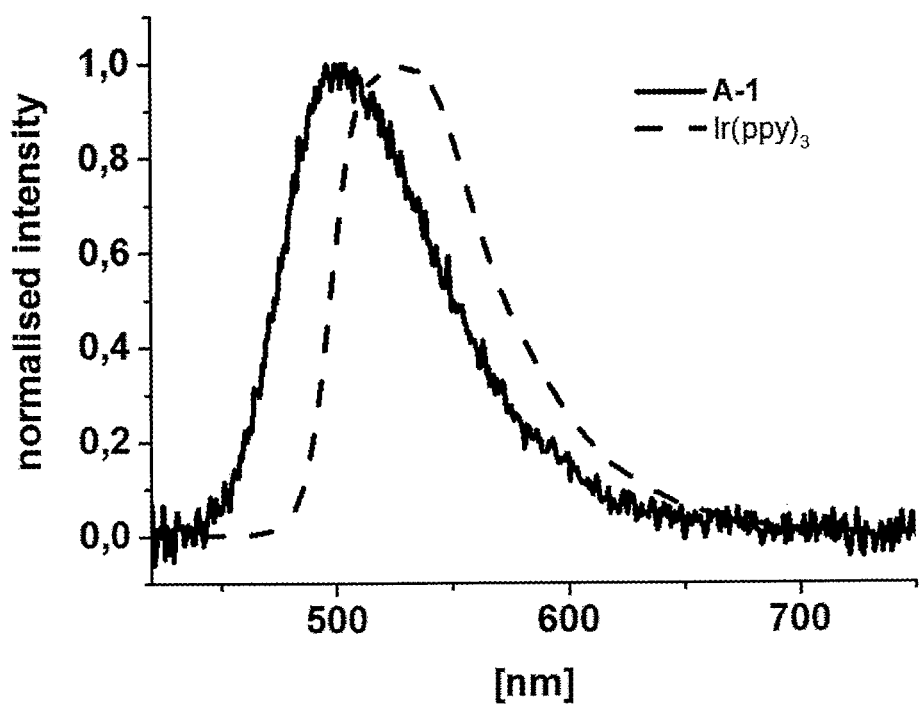

It has been found by the inventors of the present invention that the inventive metal complexes show a high photoluminescence quantum yield (PLQY) and a short lifetime of the luminescence ($\tau_v$). The inventive metal complexes shows emission having a single peak spectrum with a full width half-maximum (FWHM) of 20 nm to 140 nm, more preferably of 40 nm to 100 nm, most preferably 60 nm to 90 nm. Reference is made to FIG. 2.

Organic electronic devices, preferably OLEDs, comprising the metal complexes according to the present invention further may show improved device performance such as high quantum efficiency, high luminous efficacy, low voltage, good stabilities and/or long lifetimes.

FIG. 1: X-ray diffraction pattern of

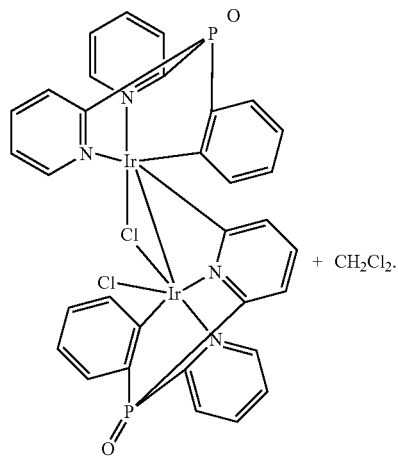

+ $CH_2Cl_2$.

FIG. 2: Photoluminescence emission spectra of poly (methyl methacrylate) (PMMA) films of metal complex (A-1) (solid line) and tris[2-phenylpyridinato-$C^2$,N]iridium (III) (Ir(ppy)$_3$) (dashed line).

The residues mentioned in the specification of the present application generally have the following preferred meanings, if not defined differently in a specific residue:

A $C_1$-$C_{18}$alkyl group, which can optionally be substituted by at least one substituent E and/or interrupted by D: preferably a $C_1$-$C_{12}$alkyl group, which can optionally be substituted by at least one substituent E and/or interrupted by D; more preferably a $C_1$-$C_8$alkyl group, which can optionally be substituted by at least one substituent E and/or interrupted by D; most preferably a $C_1$-$C_8$alkyl group, which can optionally be substituted by at least one substituent E; even more preferably an unsubstituted $C_1$-$C_8$alkyl group; further even more preferably an unsubstituted $C_1$-$C_5$alkyl group, e.g. methyl, ethyl, propyl, like n-propyl, iso-propyl, n-butyl, sec-butyl, iso-butyl, tert-butyl, or neopentyl. The alkyl groups may be linear or branched.

A $C_3$-$C_{12}$cycloalkyl group, which can optionally be substituted by at least one substituent E: preferably a $C_3$-$C_{12}$cycloalkyl group, which can optionally be substituted by at least one substituent E; more preferably a $C_3$-$C_6$cycloalkyl group, which can optionally be substituted by at least one substituent E; most preferably an unsubstituted $C_3$-$C_6$cycloalkyl group, e.g. cyclohexyl or cyclopentyl.

A $C_6$-$C_{14}$aryl group, which can optionally be substituted by at least one substituent G: preferably a $C_6$-$C_{14}$aryl group, which can optionally be substituted by one or two groups G; more preferably a phenyl group, which can optionally be substituted by one or two groups G.

A heteroaryl group comprising 3 to 11 ring atoms, which can optionally be substituted by at least one substituent G, interrupted by at least one of O, S, N and $NR^{65}$: preferably a heteroaryl group comprising 3 to 11 ring atoms, which can optionally be substituted by one or two groups G, interrupted by at least one of O, S, N and $NR^{65}$; more preferably pyridyl, methylpyridyl, pyrimidyl, pyrazinyl, carbazolyl, dibenzofuranyl, dibenzothiophenyl, indolyl, methylindolyl, benzofuranyl and benzothiophenyl, which can optionally be substituted by one, or more groups selected from a $C_1$-$C_5$alkyl group, a $C_3$-$C_6$cycloalkyl group and a $C_1$-$C_4$fluoroalkyl group; especially carbazolyl, dibenzofuranyl, dibenzothiophenyl, which can optionally be substituted by one, or more groups selected from a $C_1$-$C_5$alkyl group, a $C_3$-$C_6$cycloalkyl group and a $C_1$-$C_4$fluoroalkyl group; more especially dibenzofuranyl, dibenzothiophenyl, which can optionally be substituted by one, or more groups selected from a $C_1$-$C_4$alkyl group, and a $C_3$-$C_6$cycloalkyl group.

$R^{65}$ is a phenyl group, which can optionally be substituted by one or two $C_1$-$C_8$alkyl groups; an unsubstituted $C_1$-$C_{18}$alkyl group; or a $C_1$-$C_{18}$alkyl group, which is interrupted by —O—;

A halogen atom: preferably F or Cl, more preferably F.

A $C_1$-$C_{18}$haloalkyl group; preferably a fluoro$C_1$-$C_4$alkyl group, more preferably $CF_3$. The alkyl groups may be linear or branched.

$C_1$-$C_{18}$alkoxy groups are straight-chain or branched alkoxy groups, e.g. methoxy, ethoxy, n-propoxy, isopropoxy, n-butoxy, sec-butoxy, tert-butoxy, amyloxy, isoamyloxy or tert-amyloxy, heptyloxy, octyloxy, isooctyloxy, nonyloxy, decyloxy, undecyloxy, dodecyloxy, tetradecyloxy, pentadecyloxy, hexadecyloxy, heptadecyloxy and octadecyloxy. Examples of $C_1$-$C_8$alkoxy are methoxy, ethoxy, n-propoxy, isopropoxy, n-butoxy, sec.-butoxy, isobutoxy, tert.-butoxy, n-pentyloxy, 2-pentyloxy, 3-pentyloxy, 2,2-dimethylpropoxy, n-hexyloxy, n-heptyloxy, n-octyloxy, 1,1,3,3-tetramethylbutoxy and 2-ethylhexyloxy.

$R^{80}$, $R^{81}$ and $R^{82}$ are independently of each other a $C_1$-$C_{25}$alkyl group, which can optionally be interrupted by O; a $C_6$-$C_{14}$aryl group, which can optionally be substituted by $C_1$-$C_{18}$alkyl; or a heteroaryl group comprising 3 to 11 ring atoms, which can optionally be substituted by $C_1$-$C_{18}$alkyl; preferably, $R^{80}$, $R^{81}$ and $R^{82}$ are independently of each other a phenyl group, which can optionally be substituted by one or two $C_1$-$C_8$alkyl groups; an unsubstituted $C_1$-$C_{18}$alkyl group; or a $C_1$-$C_{18}$alkyl group, which is interrupted by —O—.

$R^7$ and $R^8$ are independently of each other H, or a $C_1$-$C_{18}$alkyl group, which can optionally be interrupted by —O—.

Metal complexes are preferred, wherein $X^1$, $X^2$ and $X^{1'}$ are N and $X^3$, $X^{2'}$ and $X^{3'}$ are C.

In another preferred embodiment the present invention is directed to metal complexes, wherein $X^1$, $X^2$ and $X^3$ are N and $X^{1'}$, $X^{2'}$ and $X^{3'}$ are C, such as, for example,

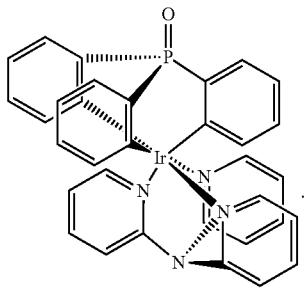

Metal complexes are preferred, wherein M is Ir.

$Y^1, Y^2, Y^3, Y^4, Y^5, Y^6, Y^7, Y^8, Y^9, Y^{10}, Y^{11}, Y^{12}, Y^{1'}, Y^{2'}, Y^{3'}, Y^{4'}, Y^{5'}, Y^{6'}, Y^{7'}, Y^{8'}, Y^{9'}, Y^{10'}, Y^{11'}$ and $Y^{12'}$ are independently of each other $CR^6$, or N, especially $CR^6$, wherein $R^6$ is defined above, or below.

Preferably, $R^6$ is independently in each occurence H, F, Cl, $NO_2$; $CF_3$; CN; a $C_1$-$C_{18}$alkyl group, a $C_1$-$C_{18}$alkoxy group, a phenyl group, a phenoxy group, or $NR^7R^8$, $R^7$ and $R^8$ are independently of each other H, or a $C_1$-$C_{18}$alkyl group, which can optionally be interrupted by —O—.

Preferably, $Z^1$ and $Z^{1'}$ are independently of each other N, P=O, C—$R^3$, or Si—$R^4$, wherein $R^3$ and $R^4$ are independently of each other a $C_1$-$C_{18}$alkyl group, a phenyl group, which is optionally substituted by a $C_1$-$C_8$alkyl group; or a $C_1$-$C_{18}$alkoxy group.

In a particularly preferred embodiment the metal complex is a compound of formula

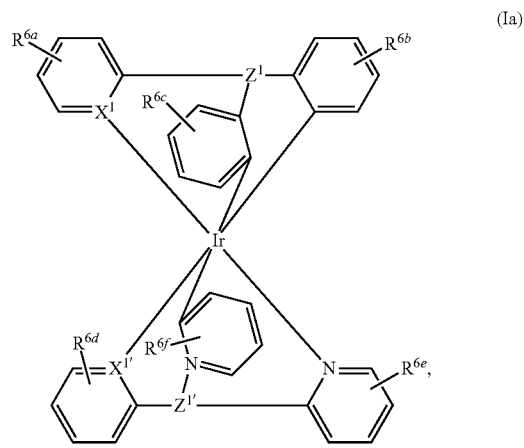

(Ia)

wherein $X^1$ and $X^{1'}$ are C, or N, $R^{6a}$, $R^{6b}$, $R^{6c}$, $R^{6d}$, $R^{6e}$ and $R^{6f}$ are independently of each other H, F, Cl, $NO_2$; $CF_3$; CN; a $C_1$-$C_{18}$alkyl group, a $C_1$-$C_{18}$alkoxy group, a phenyl group, a phenoxy group, or $NR^7R^8$, $R^7$ and $R^8$ are independently of each other H, or a $C_1$-$C_{18}$alkyl group, which can optionally be interrupted by —O—, and $Z^1$ and $Z^{1'}$ are independently of each other N, P=O, C—$R^3$, or Si—$R^4$, wherein $R^3$ and $R^4$ are independently of each other a $C_1$-$C_{18}$alkyl group, a phenyl group, which is optionally substituted by a $C_1$-$C_8$alkyl group; or a $C_1$-$C_{18}$alkoxy group.

Examples of the the metal complex of the present invention are shown below:

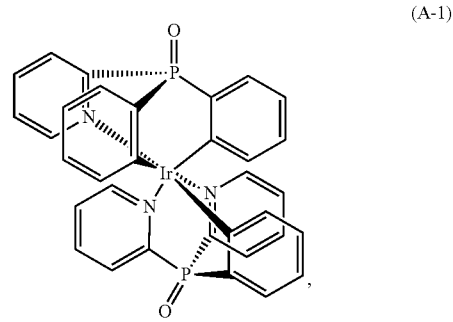

(A-1)

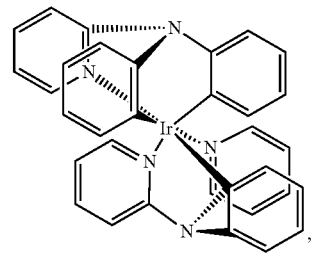

(A-2)

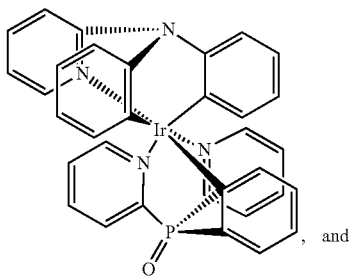

, and

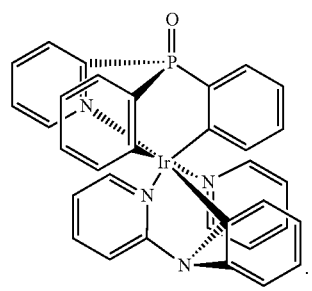

.

A process for the preparation of the metal complex of formula $L^1ML^2$(I) comprises reacting a metal complex of formula $L^1MX_3$ with a compound of formula

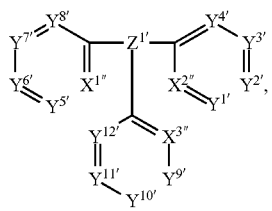

(A-3)

in a solvent in the presence of an auxiliary agent and optionally a base at elevated temperature, wherein X is Cl, Br, $C_1$-$C_8$alkyl-OH, N,N-dimethylformamide (DMF), dimethyl sulfoxide (DMSO), tetrahydrofuran (THF), or $H_2O$, $X^{1\prime\prime}$, $X^{2\prime\prime}$ and $X^{3\prime\prime}$ are CH, or N, M, $L^1$, $L^2$, $Z^{1\prime}$, $Y^{1\prime}$, $Y^{2\prime}$, $Y^{3\prime}$, $Y^{4\prime}$, $Y^{5\prime}$, $Y^{6\prime}$, $Y^{7\prime}$, $Y^{8\prime}$, $Y^{9\prime}$, $Y^{10\prime}$, $Y^{11\prime}$ and $Y^{12\prime}$ are defined above, with the proviso that at least one of $X^{1\prime\prime}$, $X^{2\prime\prime}$ and $X^{3\prime\prime}$ is CH.

The auxiliary reagent is preferably selected from $AgBF_4$, $AgNO_3$, $AgSbF_6$, $AgPF_6$, $AgAsF_6$, AgSCN, AgOCN, $Ag_2SO_4$, $AgClO_4$, $Ag(COOCF_3)$ and Ag(OTf), In general, the process of the invention is carried out in a solvent. Here, the term solvent encompasses both individual solvents and solvent mixtures. The solvent is preferably selected from glycol, DMF, N,N-Dimethylacetamide (DMA), N-Methyl-2-pyrrolidon (NMP), pyridine, toluene, xylene, chlorobenzene, dichlorobenzene, dioxane, butanone, THF, DMSO, acetonitrile, or mixtures thereof.

Optionally a base added. The base is preferably selected from $Na_2CO_3$, $K_2CO_3$, $Cs_2CO_3$, $K_3PO_4$, LiHMDS, NaHMDS, KHMDS, N(alkyl)$_3$, HN(alkyl)$_2$, pyridine, LiOtBu, NaOtBu, KOtBu, LiOAc, NaOAc, KOAc, P(aryl)$_3$, P(alkyl)$_3$, or mixtures thereof. "alkyl" is a $C_1$-$C_{18}$alkyl group, which can optionally be substituted by at least one substituent E and/or interrupted by D: preferably an unsubstituted $C_1$-$C_8$alkyl group; e.g. methyl, ethyl, propyl, like n-propyl, iso-propyl, n-butyl, sec-butyl, iso-butyl, tert-butyl, or neopentyl. The alkyl groups may be linear or branched. "aryl" is a $C_6$-$C_{14}$aryl group, which can optionally be substituted by at least one substituent G: preferably a $C_6$-$C_{14}$aryl group, which can optionally be substituted by one or two groups G; more preferably a phenyl group, The process is carried out at temperatures from 25 to 225° C., preferably from 120-200° C.

Metal complexes, wherein $X^1$, $X^2$ and $X^3$ are C, may be prepared by the process shown in the scheme below:

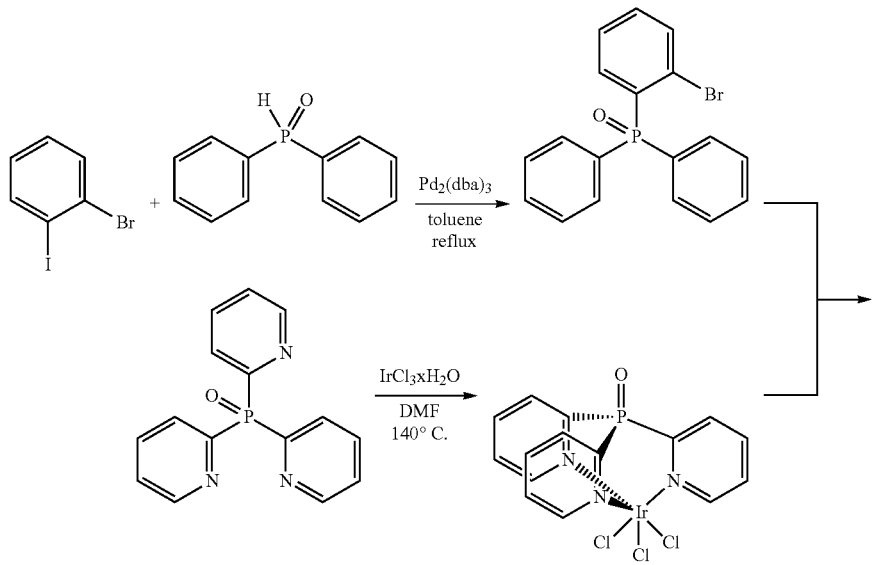

-continued

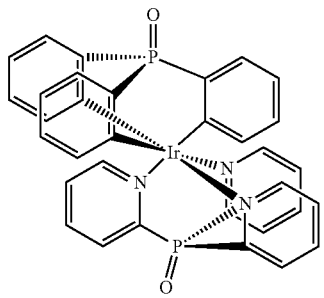

Organic Electronic Devices

The inventive metal complexes can be used in organic electronic devices. Suitable organic electronic devices are selected from organic light-emitting diodes (OLEDs), organic photovoltaic cells (OPVs), organic field-effect transistors (OFETs) and light-emitting electrochemical cells (LEECs), preference being given to OLEDs.

The inventive metal complexes are generally notable for improved device performance such as high external quantum efficiency, high luminous efficacy and low voltage, decreased lifetime of the luminescence r (higher radiation rate $k_{rad}$), reduced color-shift (e.g. CIE-y shift) with increasing doping concentration, or long device lifetime and/or excellent thermal stability. The inventive metal complexes are therefore suitable with particular preference as emitter material in OLEDs The present invention therefore concerns an organic electronic device, comprising at least one metal complex according to the present invention.

In a preferred embodiment, the organic electronic device is an OLED. The present application therefore further provides an OLED comprising at least one inventive metal complex. The inventive metal complex is used in the OLED preferably as an emitter, matrix material, charge transport material, most preferably as emitter.

The present application also provides for the use of the inventive metal complexes in OLEDs, preferably as emitter, matrix material, charge transport material, most preferably as emitter.

The at least one inventive metal complex is more preferably present in the light-emitting layer of an OLED, most preferably as emitter. The present application therefore also provides for a light-emitting layer comprising at least one inventive metal complex, preferably as emitter. More preferably, the light-emitting layer additionally comprises at least one host material.

Organic light-emitting diodes are in principle formed from a plurality of layers, e.g.:
(a) an anode,
(b) optionally a hole injection layer,
(c) optionally a hole transport layer,
(d) optionally an electron/exciton blocking layer
(e) a light-emitting layer,
(f) optionally a hole/exciton blocking layer,
(g) optionally an electron transport layer,
(h) optionally an electron injection layer, and
(i) a cathode.

It is, however, also possible that the OLED does not comprise all of the layers mentioned; for example, an OLED comprising layers (a) (anode), (e) (light-emitting layer) and (i) (cathode) is likewise suitable, in which case the functions of layers (c) (hole-transport layer) and (g) (electron-transport layer) are assumed by the adjoining layers. OLEDs comprising layers (a), (c), (e), (g) and (i) or (a), (c), (e) and (i) or layers (a), (e), (g) and (i) or (a), (b), (c), (d), (e), (g), (h) and (i) or (a), (b), (c), (e), (g), (h) and (i) or (a), (b), (c), (d), (e), (g) and (i) are likewise suitable.

The individual layers among the aforementioned layers of the OLED may in turn be formed from two or more layers. For example, the hole-transport layer may be formed from one layer, into which holes are injected from the electrode, and a layer which transports the holes away from the hole-injecting layer into the light-emitting layer. The electron-transport layer may likewise consist of a plurality of layers, for example of a layer in which electrons are injected through the electrode and a layer which receives electrons from the electron-injecting layer and transports them into the light-emitting layer. These layers mentioned are each selected according to factors such as energy level, thermal resistance and charge carrier mobility, and also energy difference of the layers mentioned with the organic layers or the metal electrodes. The person skilled in the art is capable of selecting the construction of the OLEDs such that it is matched optimally to the inventive metal complexes, preferably used as emitter substances in accordance with the invention.

In order to obtain particularly efficient OLEDs, the HOMO (highest occupied molecular orbital) of the hole-transport layer should be aligned to the work function of the anode, and the LUMO (lowest unoccupied molecular orbital) of the electron-transport layer should be aligned to the work function of the cathode.

Suitable materials for the aforementioned layers (anode, cathode, hole and electron injection materials, hole and electron transport materials and hole and electron blocker materials, matrix materials, fluorescence and phosphorescence emitters) are known to those skilled in the art and are specified, for example, in H. Meng, N. Herron, *Organic Small Molecule Materials for Organic Light-Emitting Devices in Organic Light-Emitting Materials and Devices*, eds: Z. Li, H. Meng, Taylor & Francis, 2007, Chapter 3, pages 295 to 411 as well as in US2012/0104422, D. J. Gaspar, E Polikarpov, OLED Fundamentals: Materials, Devices, and Processing of Organic Light-Emitting Diodes, CRC Press, Taylor & Francis, 2015,and Z. R. Li, Organic Light-Emitting Materials and Devices, CRC Press, Taylor & Francis, 2015.

In addition, it is possible that some or all of the layers (b) to (h) have been surface-treated in order to increase the efficiency of charge carrier transport. The selection of the materials for each of the layers mentioned is preferably determined by obtaining an OLED having a high efficiency.

The inventive metal complexes are preferably used as emitter molecules and/or matrix materials in the light-emitting layer (e). The inventive metal complexes may—in addition to use as emitter molecules and/or matrix materials in the light-emitting layer (e) or instead of use in the light-emitting layer—also be used as a charge transport material in the hole-transport layer (c) or in the electron-transport layer (g) and/or as a charge blocker, preference being given to use as a charge transport material in the hole-transport layer (c) (hole transport material).

Light-Emitting Layer (e)

Emitter

Suitable emitter materials for OLEDs are known by a person skilled in the art. The light-emitting layer preferably comprises at least one phosphorescent emitter. Phosphorescent emitters are preferred because of the higher luminescent efficiencies associated with such materials. The light-emitting layer preferably also comprises at least one host material. Preferably, the host material is capable of transporting electrons and/or holes, doped with an emitting material that may trap electrons, holes, and/or excitons, such that excitons relax from the emissive material via a photoemissive mechanism. In a preferred embodiment, the light emitting layer comprises the emitter and two host materials. In this case the two host materials both contribute to the transport of electrons and/or holes. By adjusting the mixing ratio of the two host materials, the optimal charge carrier balance and thus the optimal device performance in terms of voltage, lifetime, efficiency and/or color can be achieved.

Preferably, the inventive metal complexes are used as emitter. The light-emitting layer (e) may comprise one or more of the inventive metal complexes as emitter material. Suitable and preferred inventive metal complexes are mentioned above. It is also possible that the light-emitting layer comprises in addition to at least one inventive metal complex one or more further emitters.

The light-emitting layer preferably comprises beside at least one emitter material (suitable emitter materials are mentioned above), preferably at least one metal complex according to the present invention, at least one host material.

Suitable host materials are known by a person skilled in the art. Preferred host materials are mentioned below.

Host

For efficient light emission the triplet energy of the host material has to be about 0.2 eV larger than the triplet energy of the phosphorescent emitter (preferably the metal complex according to the present invention) used. Hence, all host materials fulfilling this requirement are, in principle, suitable as host compound.

Suitable host materials for phosphorescent emitters are, for example, described in EP2363398A1, WO2008/031743, WO2008/065975, WO2010/145991, WO2010/047707, US2009/0283757, US2009/0322217, US2010/0001638, WO2010/002850, US2010/0060154, US2010/0060155, US2010/0076201, US2010/0096981, US2010/0156957, US2011/186825, US2011/198574, US2011/0210316, US2011/215714, US2011/284835, and WO2012/045710. Further suitable host materials for phosphorescent green to yellow emitters are, for example, described in WO2012/004765 and US2011/0006670 (e.g. SH-2 Host), US2014/0001446 and WO2015/014791. The host material may be a compound having hole-transporting property and/or an organic compound having electron-transporting property. In principle, any organic compound or organometallic compound having hole-transporting property or having electron-transporting property and sufficient triplet energy can be used as host in the light-emitting layer. In a preferred embodiment, it is also possible to combine an organic compound or organometallic compound having both hole- and electron-transporting property and an organic compound or organometallic compound having either hole- or electron-transporting properties as hosts. Both materials can be processed from separate sources or as one pre-mixed host-compound.

Examples of organic compounds which can be used for the host material include a carbazole derivative such as 4,4'-di(carbazolyl)biphenyl (abbreviation: CBP), 1,3-bis (carbazolyl)benzene (abbreviation: mCP) or 1,3,5-tris(N-carbazolyl)benzene (abbreviation: TCzB), =DNTPD.

Examples of organometallic compounds which can be used for the host material include iridium carbene complexes. Suitable iridium carbene complexes are, for example, iridium carbene complexes as described in WO2005/019373A2, WO2006/056418 A2, WO2007/115970, WO2007/115981, WO2008/000727, WO2012/121936A2, US2012/0305894A1, and WO2012/172482A1. Examples of suitable iridium carbene complexes are Ir(D-PBIC)$_3$ with the formula:

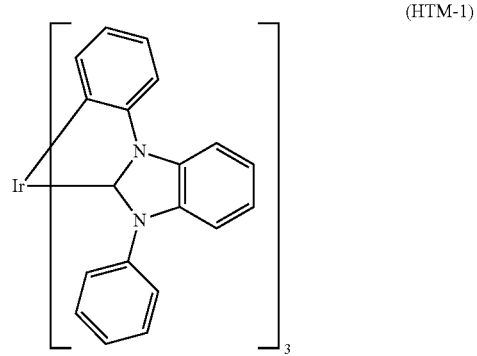

(HTM-1)

and Ir(ABIC)$_3$ with the formula:

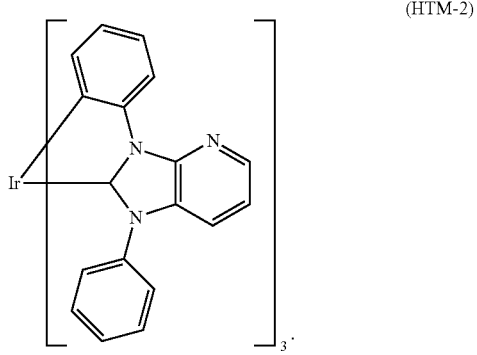

(HTM-2)

Further suitable host materials are the compounds described in WO2010/079051 (in particular pages on 19 to 26 and in the tables on pages 27 to 34, pages 35 to 37 and pages 42 to 43).

Also preferred as host compounds in the OLED and in the light-emitting layer of the present invention are the compounds mentioned in WO2012/130709; WO2013/050401; WO2014/009317; WO2014/044722; and the non-published European Patent Application EP13191100.0.

Further preferred host materials are binary host systems as described in WO2011/136755; the hosts described in WO2013/022419 and WO2013/112557; triphenylene derivatives for example as described in WO2010/028151, WO2010/002850, WO2010/0056669, US2010/0244004, US2011/0177641, US2011/022749, WO2011/109042, and WO2011/137157; azaborinine compounds for example as described in WO2011/143563; bicarbazole compounds for example as described in WO2012/023947; carbazolephenyl-pyridine, -pyrimidine and -triazine compounds for example as described in WO2012/108879; biscarbazolephenyl-pyridine, -pyrimidine and -triazine compounds for example as described in WO2012/108881; dibenzoquinoxaline compounds for example as described in US2011/0210316; triazole derivatives for example as described in US2011/0285276 and US2012/0025697; benzimidazole derivatives for example as described in US2011/0147792; heterocyclic compounds for example as described in US2012/0061651; phenanthrene derivatives for example as described in US2012/0104369; benzoxazole derivatives for example as described in US2012/0132896; oxazole derivatives for example as described in US2012/0130081; and carbazole-benzimidazole derivatives for example as described in US2012/0133274.

Further preferred host materials are described in US2011/0006670 (the SH-2 host is for example mentioned therein).

Especially suitable host materials are for example host materials described in WO2013/112557 having the following general formula:

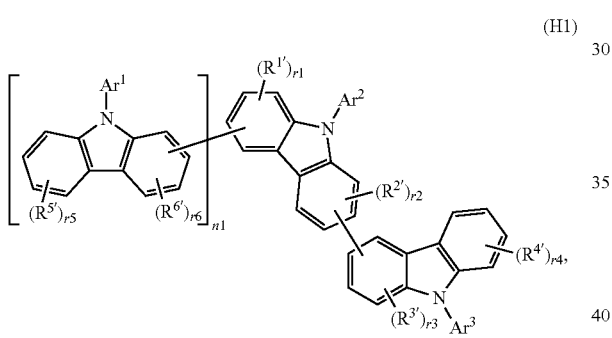

(H1)

wherein $R^{1'}$, $R^{2'}$, $R^{3'}$, $R^{4'}$, $R^{5'}$, and $R^{6'}$ may be the same or different fluorine atom, chlorine atom, a deuterium atom, a cyano group, a trifluoromethyl group, a nitro group, linear or branched $C_1$-$C_6$alkyl group, $C_5$-$C_{10}$cyclo-alkyl group, linear or branched $C_1$-$C_6$alkoxy group, $C_5$-$C_{10}$cyclo-alkoxy group, substituted or unsubstituted aromatic hydrocarbon group, substituted or unsubstituted aromatic heterocyclic group, substituted or unsubstituted condensed polycyclic aromatic group, r1, r4, r5 is 0, 1, 2, 3, or 4,
r2, r3, r6 is 0, 1, 2 or 3,
n1 is 0 or 1, and $Ar^1$, $Ar^2$, and $Ar^3$ may be the same or different, substituted or unsubstituted aromatic hydrocarbon group, substituted or unsubstituted aromatic heterocyclic group, substituted or unsubstituted condensed polycyclic aromatic group, deuterium substituted aromatic hydrocarbon group, deuterium substituted aromatic heterocyclic group, or deuterium substituted condensed polycyclic aromatic group.

When $Ar^1$, $Ar^2$, or $Ar^3$ is a substituted aromatic hydrocarbon group, a substituted aromatic heterocyclic group, or a substituted polycyclic aromatic group, the substitution groups can be any non-carbon or carbon-containing functional group, such as, an aromatic hydrocarbon group, an aromatic heterocyclic group or a polycyclic aromatic group.

For example, the substitution group on the aromatic ring structure of $Ar^1$, $Ar^2$, or $Ar^3$ can be

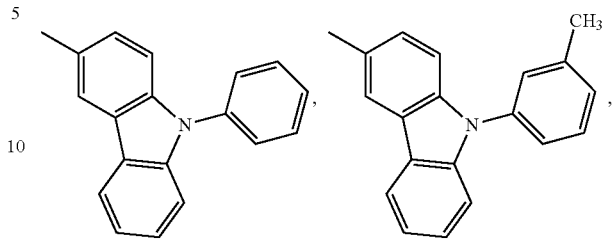

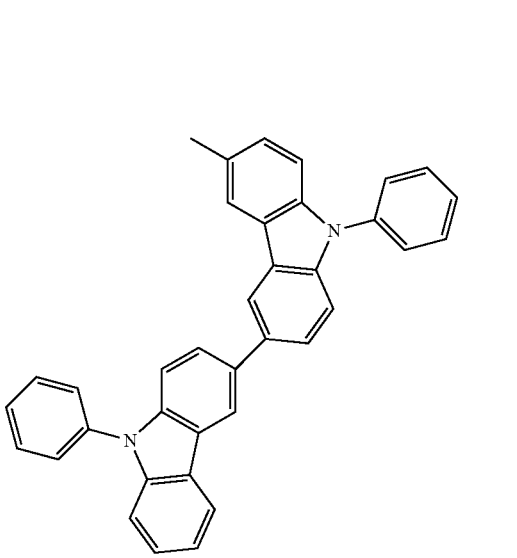

or the like.

Especially suitable are the compounds (H1-1), (H1-2), (H1-7) as mentioned below and the compounds (H1-3), (H1-4), (H1-5), (H1-6), (H1-8), (H1-9), (H1-10), (H1-11), (H1-12), (H1-13), (H1-14), (H1-15), (H1-16) and (H1-17) as described in WO 2013/112557.

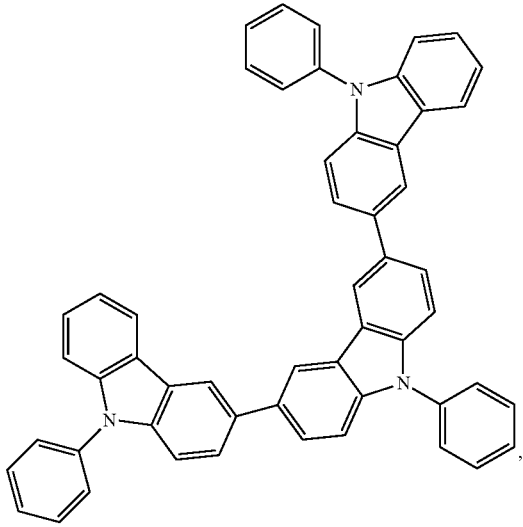

(H1-1)

-continued

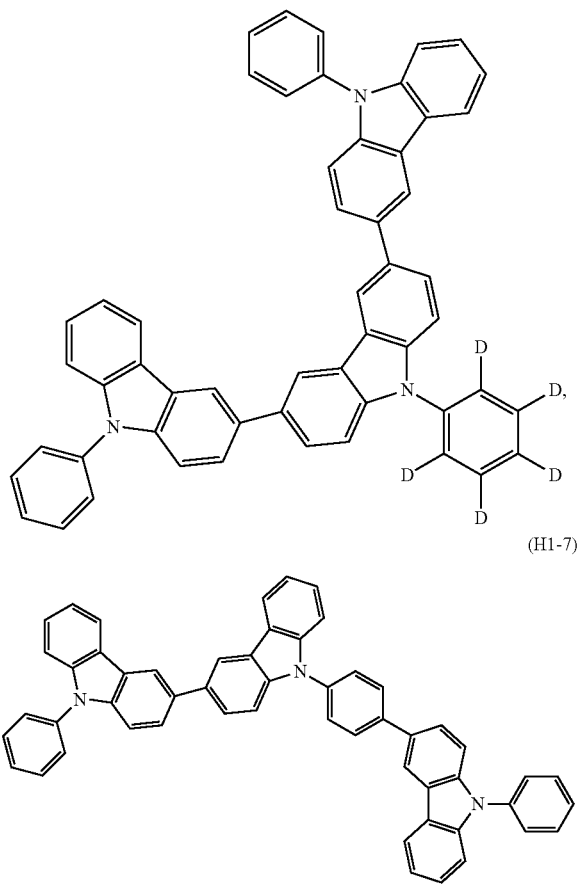

(H1-2)

(H1-7)

Further suitable host materials—which may be employed together with the host material mentioned before—are host materials containing at least one of the following groups in the molecule:

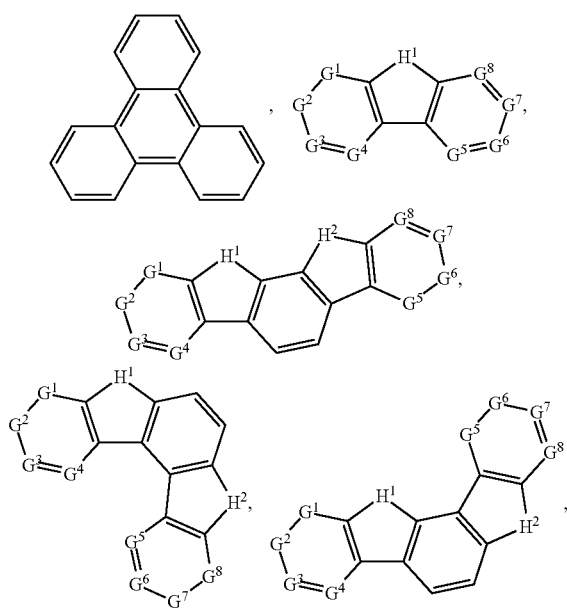

-continued

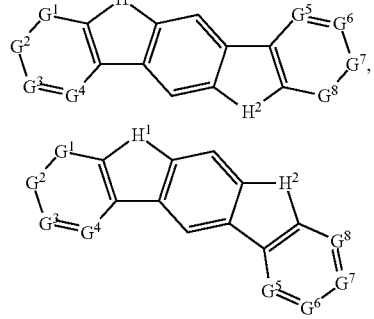

wherein $G^1$ to $G^8$ is selected from C or N; and wherein $H^1$ and $H^2$ is S or O.

The groups mentioned above may be unsubstituted or substituted by an unfused substituent independently selected from the group consisting of $C_nH_{2n+1}$, $OC_nH_{2n+1}$, $OAr_1$, $N(C_nH_{2n+1})_2$, $N(Ar_1)(Ar_2)$, $CH=CH-C_nH_{2n+1}$, $C\equiv CHC_nH_{2n+1}$, $A_1$, $Ar_1$-$Ar_2$, $C_nH_{2n-Ar1}$, wherein n is 1, 2, 3, 4, 5, 6, 7, 8, 9, or 10, and wherein $Ar_1$ and $Ar_2$ are independently selected from the group consisting of benzene, biphenyl, naphthalene, triphenylene, carbazole, and heteroaromatic analogs thereof.

Further suitable host compounds are compounds comprising a triphenylene containing benzo-fused thiophene. A combination of benzo-fused thiophenes and triphenylene as hosts in OLEDs may be beneficial. Therefore combining these two moieties in one molecule may offer improved charge balance which may improve device performance in terms of lifetime, efficiency and low voltage. Different chemical linkage of the two moieties can be used to tune the properties of the resulting compound to make it the most appropriate for a particular phosphorescent emitter, device architecture, and/or fabrication process. For example, m-phenylene linkage is expected to result in higher triplet energy and higher solubility whereas p-phenylene linkage is expected to result in lower triplet energy and lower solubility.

Similar to the characterization of benzo-fused thiophenes, benzo-fused furans are also suitable host materials. Examples of benzo-fused furans include benzofuran and dibenzofuran. Therefore, a material containing both triphenylene and benzofuran may be advantageously used as host material in OLEDs. A compound containing both of these two groups may offer improved electron stabilization which may improve device stability and efficiency with low voltage. The properties of the triphenylene containing benzofuran compounds may be tuned as necessary by using different chemical linkages to link the triphenylene and the benzofuran.

Benzo-fused furans are benzofurans and dibenzofurans. Benzo-fused thiophenes are benzothiophenes and dibenzothiophenes.

The benzo-fused thiophene and benzo-fused furans mentioned above may be unsubstituted or substituted for example by one or more unfused substituents independently selected from the group consisting of $C_nH_{2n+1}$, $OC_nH_{2n+1}$, $OAr_1$, $N(C_nH_{2n+1})_2$, $N(Ar_1)(Ar_2)$, $CH=CH-C_nH_{2n+1}$, $C\equiv CHC_nH_{2n+1}$, $A_1$, $Ar_1$-$Ar_2$, $C_nH_{2n-Ar1}$, wherein n is 1, 2, 3, 4, 5, 6, 7, 8, 9, or 10, and wherein $Ar_1$ and $Ar_2$ are independently selected from the group consisting of benzene, biphenyl, naphthalene, triphenylene, carbazole, and heteroaromatic analogs thereof.

The substituents of the compounds described above are unfused such that the substituents are not fused to the triphenylene, benzo-fused furan or benzo-fused thiophene moieties of the compound. The substituents may optionally be inter-fused (i.e. fused to each other).

The benzo-fused thiophene and benzo-fused furans mentioned above are for example described in WO2013/112557 and in WO2009/021126.

Further suitable host materials for phosphorescent green emitters are mentioned in US2013/0181190, especially in table 3, and US2013/0119354, especially in table 4.

Specific examples of organic compounds which can be used for the host material include compounds such as

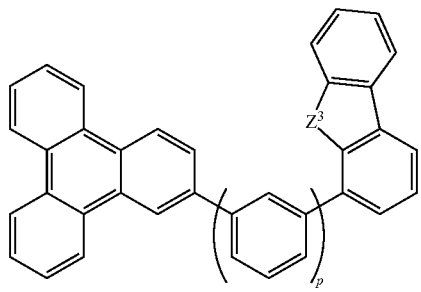

wherein $Z^3$ is O or S and p is 0 or 1, such as

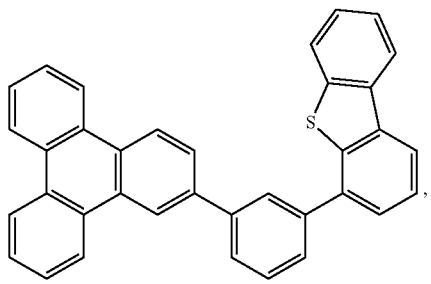

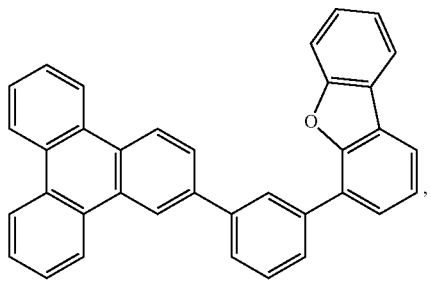

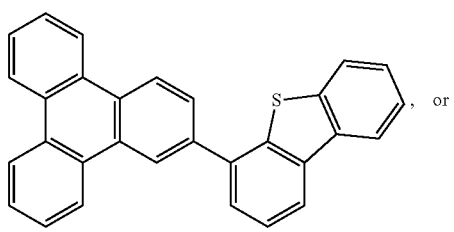, or

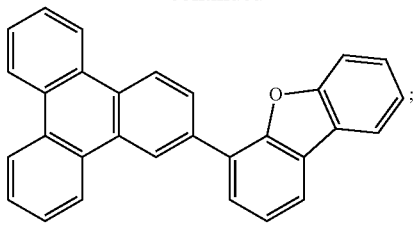;

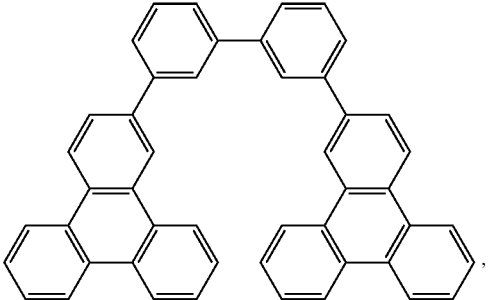,

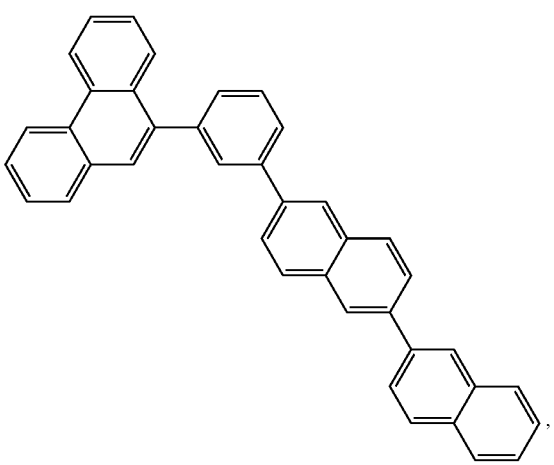,

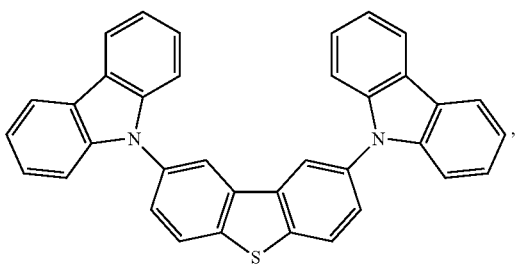,

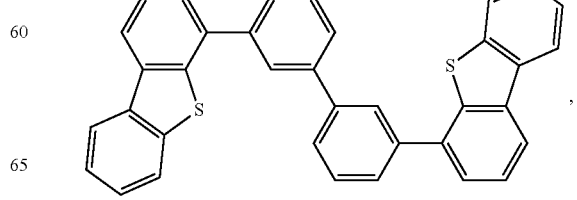,

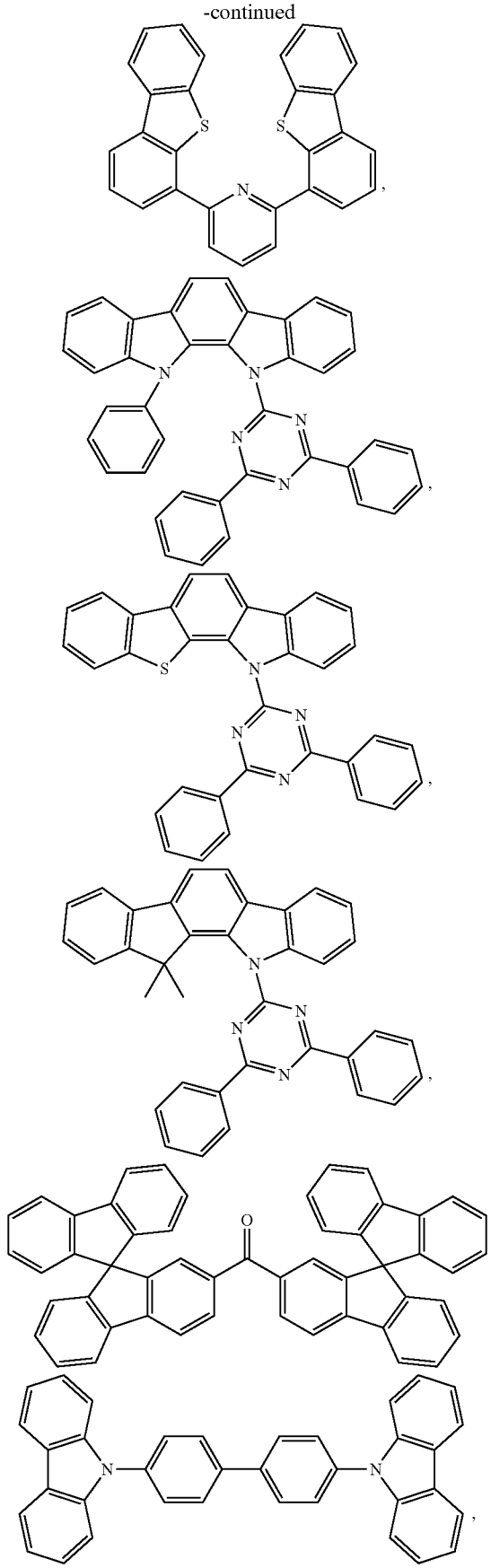
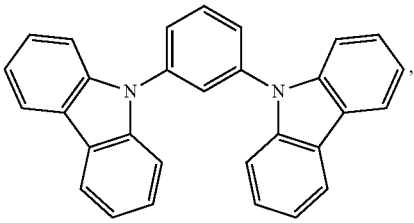
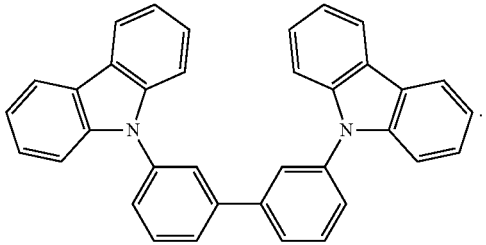
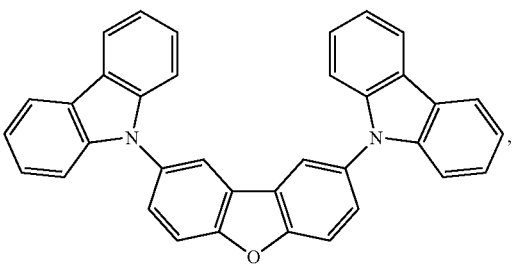
Further specific examples of organic compounds which can be used for the host material include the following compounds
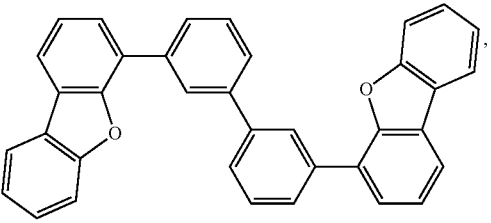
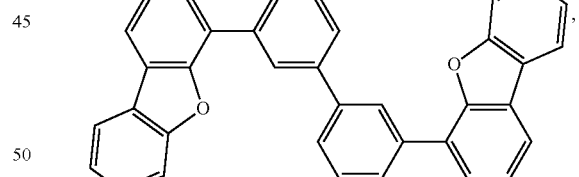
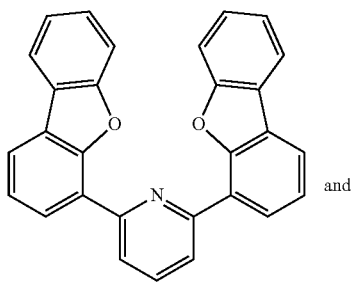
and -continued

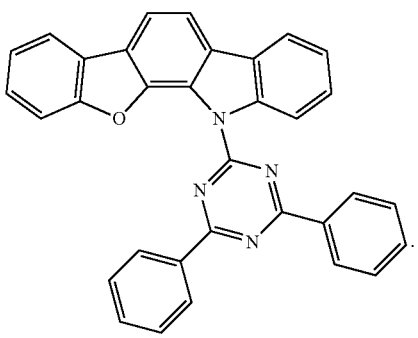

The host compound can be one compound or it can be a mixture of two or more compounds. Suitable mixtures are for example the binary hosts systems as described in WO2011/136755 and WO2013/112557.

A further suitable host material for the emitters of the present invention is mentioned in US2012/0235123 and US2011/0279020. A typical and preferred host material described in the documents mentioned before is

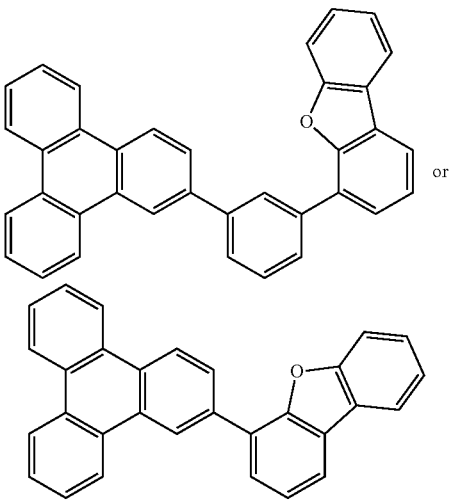

combined with

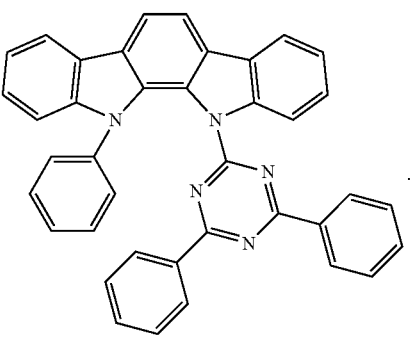

Additionally, as mentioned before, co-host systems are suitable as host material for the emitters of the present invention. A suitable co-host system is exemplified below. It is clear for a person skilled in the art that also similar co-host systems are suitable.

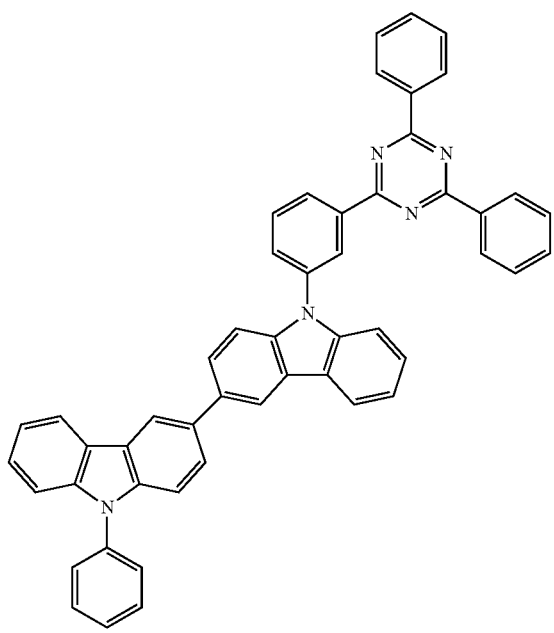 [SMILES: c1ccc(-c2nc(-c3ccccc3)nc(-c3cccc(-n4c5ccccc5c5cc(-c6ccc7c(c6)c6ccccc6n7-c6ccccc6)ccc54)c3)n2)cc1]

In a preferred embodiment, the light-emitting layer (e) comprises the emitter in an amount of 2 to 40% by weight, preferably 5 to 35% by weight, more preferably 5 to 20% by weight and the host compound in an amount of 60 to 98% by weight, preferably 65 to 95% by weight, more preferably 80 to 95% by weight, where the amount of the phosphorescent emitter and the host compound adds up to a total of 100% by weight. The emitter may be one emitter or a combination of two or more emitters. The host may be one host or a combination of two or more hosts.

In a preferred embodiment, in case of the use of two host compounds they are mixed in a ratio of 1:1 to 1:30, more preferably 1:1 to 1:7, most preferably 1:1 to 1:3.

Anode (a)

The anode is an electrode which provides positive charge carriers. It may be composed, for example, of materials which comprise a metal, a mixture of different metals, a metal alloy, a metal oxide or a mixture of different metal oxides. Alternatively, the anode may be a conductive polymer. Suitable metals comprise the metals of groups 11, 4, 5 and 6 of the Periodic Table of the Elements, and also the transition metals of groups 8 to 10. When the anode is to be transparent, mixed metal oxides of groups 12, 13 and 14 of the Periodic Table of the Elements are generally used, for example indium tin oxide (ITO). It is likewise possible that the anode (a) comprises an organic material, for example polyaniline, as described, for example, in Nature, Vol. 357, pages 477 to 479 (Jun. 11, 1992). Preferred anode materials include conductive metal oxides, such as indium tin oxide (ITO) and indium zinc oxide (IZO), aluminum zinc oxide (AlZnO), and metals. Anode (and substrate) may be sufficiently transparent to create a bottom-emitting device. A preferred transparent substrate and anode combination is commercially available ITO (anode) deposited on glass or plastic (substrate). A reflective anode may be preferred for some top-emitting devices, to increase the amount of light emitted from the top of the device. At least either the anode or the cathode should be at least partly transparent in order to be able to emit the light formed. Other anode materials and structures may be used.

Hole Injection Layer (b)

Generally, injection layers are comprised of a material that may improve the injection of charge carriers from one layer, such as an electrode or a charge generating layer, into an adjacent organic layer. Injection layers may also perform a charge transport function. The hole injection layer may be any layer that improves the injection of holes from anode into an adjacent organic layer. A hole injection layer may comprise a solution deposited material, such as a spin-coated polymer, or it may be a vapor deposited small molecule material, such as, for example, CuPc or MTDATA. Polymeric hole-injection materials can be used such as poly(N-vinylcarbazole) (PVK), polythiophenes, polypyrrole, polyaniline, self-doping polymers, such as, for example, sulfonated poly(thiophene-3-[2[(2-methoxyethoxy)ethoxy]-2,5-diyl) (Plexcore® OC Conducting Inks commercially available from Plextronics), and copolymers such as poly(3,4-ethylenedioxythiophene)/poly(4-styrenesulfonate) also called PEDOT/PSS. Further suitable hole injection materials are mentioned in US2013/0181190, especially in table 3, and US2013/0119354, especially in table 4.

It is possible to use as hole injection materials p-doped layers. Suitable p-dopants are mentioned below concerning the hole transport layer. Examples for suitable p-dopants are MoO₃, F4-TCNQ or NDP-9. It is further possible to use layers of p-dopants itself. Suitable p-dopants are mentioned below concerning the hole transport layer. Examples for suitable p-dopants are MoO₃, F4-TCNQ or NDP-9.

Further suitable hole injection materials are described in US2006/0188745, US2006/0240280 and US2007/0092755, whereby the following material is an example for a preferred hole injection material:

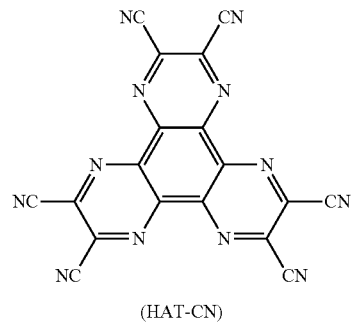 [SMILES: N#Cc1nc2c3nc(C#N)c(C#N)nc3c3nc(C#N)c(C#N)nc3c2nc1C#N]
(HAT-CN)

Further suitable hole injection materials are described in US2010/0219400, US2015/0073142 and US2015/0102331, whereby the following material is an example for a preferred hole injection material:

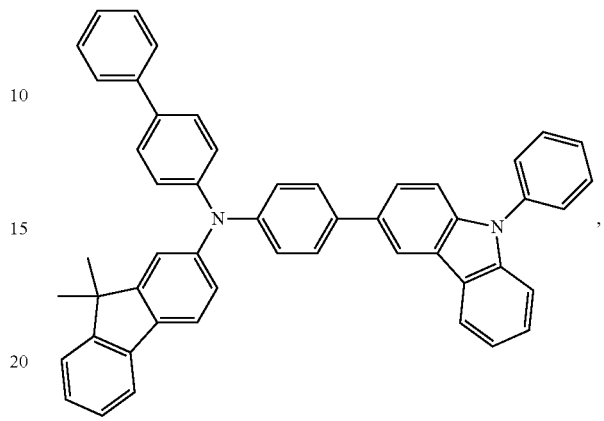

preferably doped with MoO₃, F4-TCNQ or NDP-9, more preferably doped with NDP-9.

The dopant NDP-9 is commercially available and for example described in EP 2 180 029. Further suitable hole injection materials are the following materials:

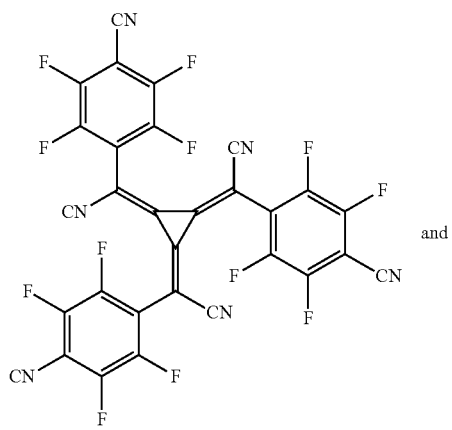
and
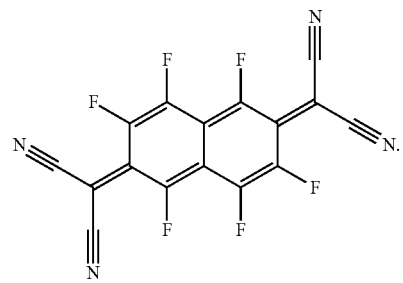

Further compounds suitable as hole injection material are for example mentioned in US2010/0044689 and US2014/0217392, e.g. the following compound

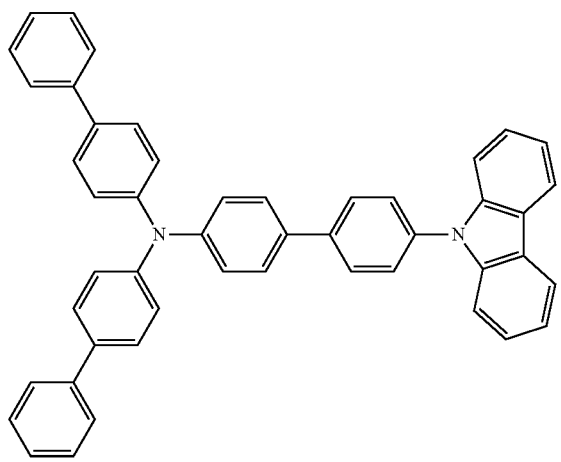 [SMILES: c1ccc(-c2ccc(N(c3ccc(-c4ccccc4)cc3)c3ccc(-c4ccc(-n5c6ccccc6c6ccccc65)cc4)cc3)cc2)cc1]

doped with a p-dopant. Suitable p-dopants are mentioned below concerning the hole transport layer. Examples for suitable p-dopants are MoO$_3$, F4-TCNQ or NDP-9.

Further compounds suitable as hole injection material are for example mentioned in US2010/0219400, US2015/0073142 and US2015/0102331, e.g. the following compound

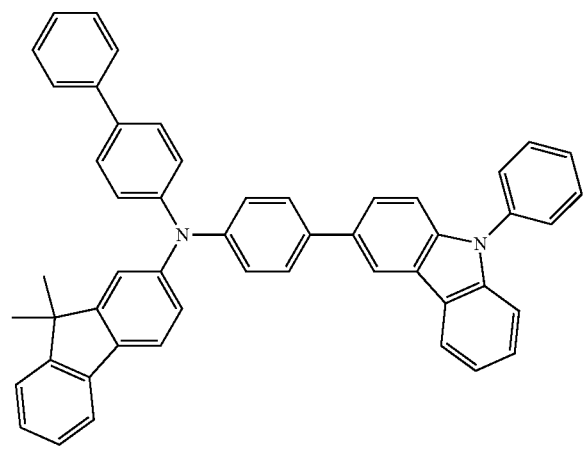 [SMILES: CC1(C)c2ccccc2-c2ccc(N(c3ccc(-c4ccccc4)cc3)c3ccc(-c4ccc5c(c4)c4ccccc4n5-c4ccccc4)cc3)cc21]

doped with a p-dopant. Suitable p-dopants are mentioned below concerning the hole transport layer. Examples for suitable p-dopants are MoO$_3$, F4-TCNQ or NDP-9.

Further compounds suitable as hole injection material are for example mentioned in US2008/0014464, e.g. the following compound

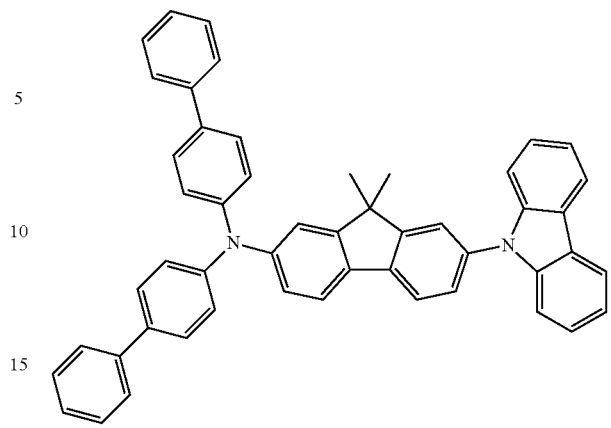

doped with a p-dopant. Suitable p-dopants are mentioned below concerning the hole transport layer. Examples for suitable p-dopants are MoO$_3$, F4-TCNQ or NDP-9 (N,N'-Di(1-naphthyl)-N,N'-diphenyl-(1,1'-biphenyl)-4,4'-diamine).

F4-TCNQ:

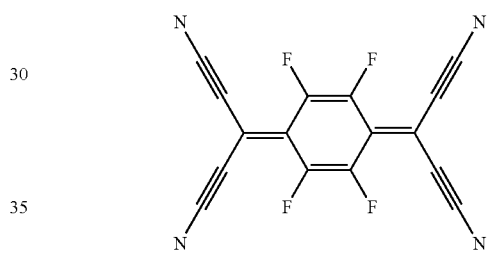

In addition to the hole injection materials mentioned above, the materials mentioned as hole transport materials in the hole transport layer are also useful as hole injection materials, especially in combination with a p-dopant, for example in combination with MoO$_3$, F4-TCNQ or NDP-9. Further suitable p-dopants are mentioned below (see hole transport layer (c)).

Hole Transport Layer (c)

Either hole-transporting molecules or polymers may be used as the hole transport material. Suitable hole transport materials for layer (c) of the inventive OLED are disclosed, for example, in Kirk-Othmer Encyclopedia of Chemical Technology, 4th Edition, Vol. 18, pages 837 to 860, 1996, US20070278938, US2008/0106190, US2011/0163302 (triarylamines with (di)benzothiophen/(di)benzofuran; Nan-Xing Hu et al. Synth. Met. 111 (2000) 421 (indolocarbazoles), WO2010/002850 (substituted phenylamine compounds), WO2012/16601 (in particular the hole transport materials mentioned on pages 16 and 17 of WO2012/16601), US2013/0181190, especially in table 3, and US2013/0119354, especially in table 4. Further suitable hole transport materials are mentioned in US20120223296. Combination of different hole transport material may be used. Reference is made, for example, to WO2013/022419, wherein
(HTL1-1)
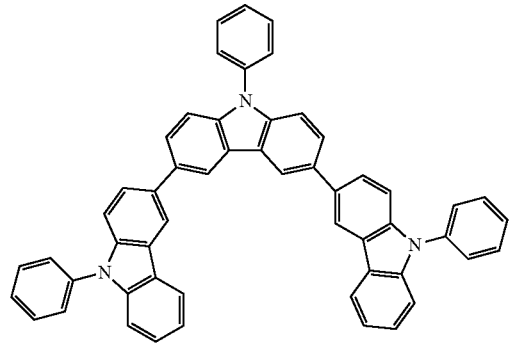
and
(HTL2-1)
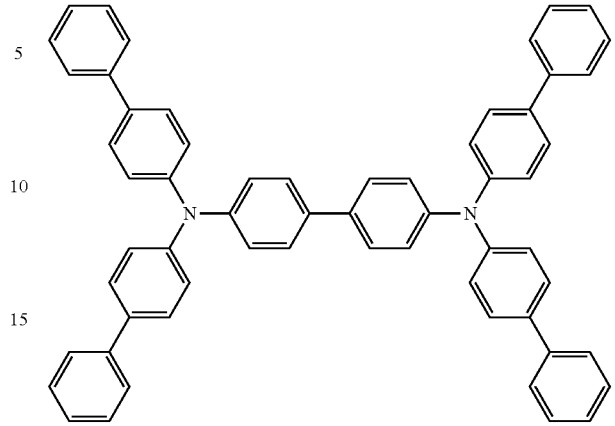
constitute the hole transport layer.
Customarily used hole-transporting molecules are selected from the group consisting of
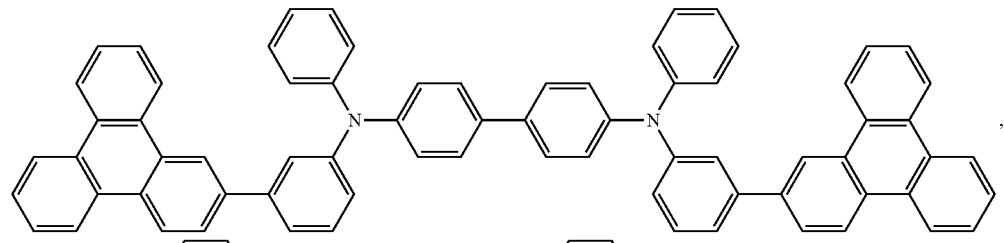
,
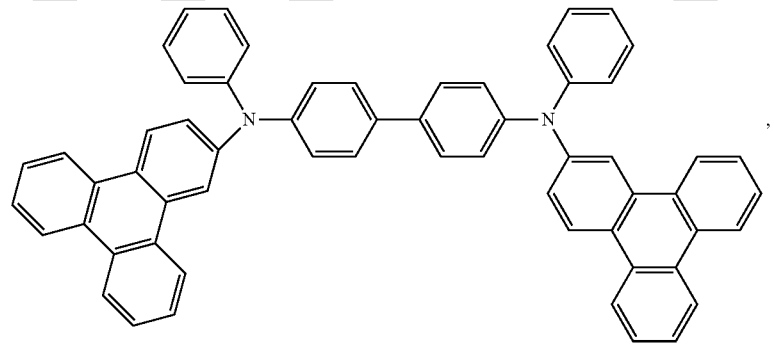
,
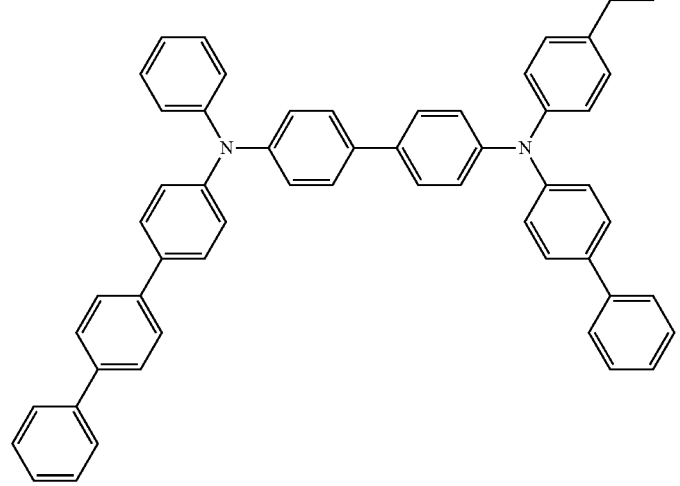

(4-phenyl-N-(4-phenylphenyl)-N-[4-[4-(N-[4-(4-phenyl-phenyl)phenyl]anilino)phenyl]phenyl]aniline),

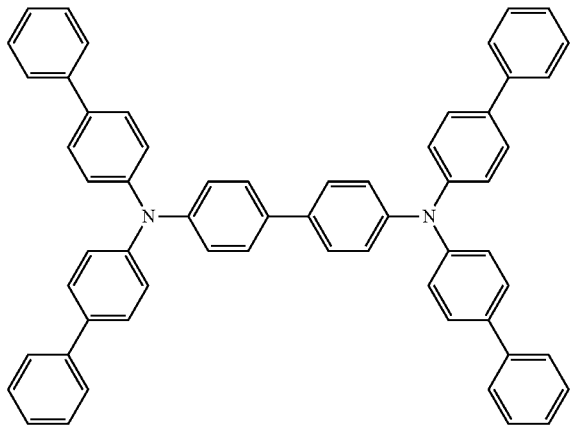 [SMILES: c1ccc(-c2ccc(N(c3ccc(-c4ccccc4)cc3)c3ccc(-c4ccc(N(c5ccc(-c6ccccc6)cc5)c5ccc(-c6ccccc6)cc5)cc4)cc3)cc2)cc1]

(4-phenyl-N-(4-phenylphenyl)-N-[4-[4-(4-phenyl-N-(4-phenylphenyl)anilino)phenyl]phenyl]aniline),

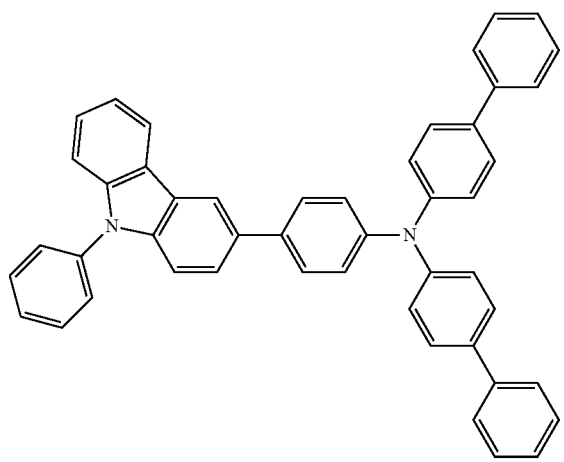 [SMILES: c1ccc(-c2ccc(N(c3ccc(-c4ccccc4)cc3)c3ccc(-c4ccc5c(c4)c4ccccc4n5-c4ccccc4)cc3)cc2)cc1]

(4-phenyl-N-[4-(9-phenylcarbazol-3-yl)phenyl]-N-(4-phenylphenyl)aniline),

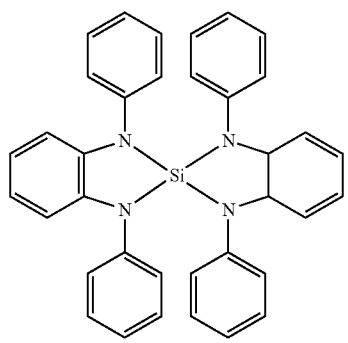 [SMILES: C1=CC2C(C=C1)N(c1ccccc1)[Si]1(N(c3ccccc3)c3ccccc3N1c1ccccc1)N2c1ccccc1]

(1,1',3,3'-tetraphenylspiro[1,3,2-benzodiazasilole-2,2'-3a,7a-dihydro-1,3,2-benzodiazasilole]),

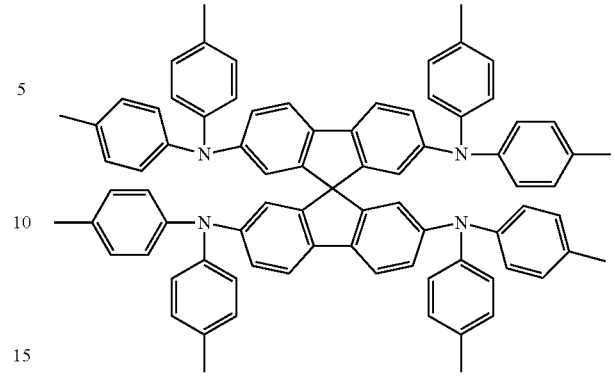

(N2,N2,N2',N2',N7,N7,N7',N7'-octa-kis(p-tolyl)-9,9'-spirobi[fluorene]-2,2',7,7'-tetramine), 4,4'-bis[N-(1-naphthyl)-N-phenyl-amino]biphenyl (α-NPD), N,N'-diphenyl-N,N'-bis(3-methylphenyl)-[1,1'-biphenyl]-4,4'-diamine (TPD), 1,1-bis[(di-4-tolylamino)phenyl]cyclohexane (TAPC), N,N'-bis(4-methylphenyl)-N,N'-bis(4-ethylphenyl)-[1,1'-(3, 3'-dimethyl)-biphenyl]-4,4'-diamine (ETPD), tetrakis(3-methylphenyl)-N,N,N',N'-2,5-phenylenediamine (PDA), α-phenyl-4-N,N-diphenylaminostyrene (TPS), p-(diethylamino)benzaldehyde diphenyl-hydrazone (DEH), triphenylamine (TPA), bis[4-(N,N-diethylamino)-2-methylphenyl](4-methylphenyl)methane (MPMP), 1-phenyl-3-[p-(diethylamino)styryl]-5-[p-(diethylamino)phenyl] pyrazoline (PPR or DEASP), 1,2-trans-bis(9H-carbazol-9-yl)-cyclobutane (DCZB), N,N,N',N'-tetrakis(4-methylphenyl)-(1,1'-biphenyl)-4,4'-diamine (TTB), fluorine compounds such as 2,2',7,7'-tetra(N,N-di-tolyl)amino-9,9-spirobifluorene (spiro-TTB), N,N'-bis(naphthalen-1-yl)-N,N'-bis(phenyl)-9,9-spirobifluorene (spiro-NPB) and 9,9-bis (4-(N,N-bis-biphenyl-4-yl-amino)phenyl-9H-fluorene, benzidine compounds such as N,N'-bis(naphthalen-1-yl)-N,N'-bis(phenyl)-benzidine and porphyrin compounds such as copper phthalocyanines. In addition, polymeric hole-injection materials can be used such as poly(N-vinylcarbazole) (PVK), polythiophenes, polypyrrole, polyaniline, self-doping polymers, such as, for example, sulfonated poly(thiophene-3-[2[(2-methoxyethoxy)ethoxy]-2,5-diyl) (Plexcore® OC Conducting Inks commercially available from Plextronics), and copolymers such as poly(3,4-ethylenedioxythiophene)/poly(4-styrenesulfonate) also called PEDOT/PSS.

In a preferred embodiment it is possible to use metal carbene complexes as hole transport materials. Suitable carbene complexes are, for example, carbene complexes as described in WO2005/019373A2, WO2006/056418 A2, WO2007/115970, WO2007/115981, WO2008/000727, WO2012/121936A2, US2012/0305894A1, and WO2012/172482A1. One example of a suitable carbene complex is Ir(DPBIC)$_3$ (HTM-1). Another example of a suitable carbene complex is Ir(ABIC)$_3$ (HTM-2). The formulae of (HTM-1) and (HTM-2) are mentioned above.

Further compounds suitable as hole transport material are for example mentioned in US2010/0044689 and US2014/0217392, e.g. the following compound

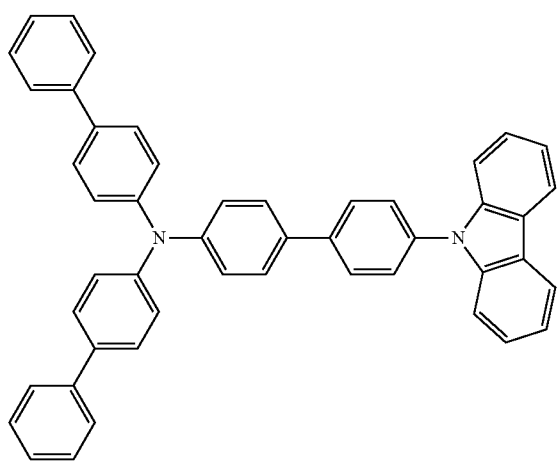 [SMILES: c1ccc(-c2ccc(N(c3ccc(-c4ccccc4)cc3)c3ccc(-c4ccc(-n5c6ccccc6c6ccccc65)cc4)cc3)cc2)cc1]

The compounds are employed in the hole transport layer in doped or undoped form. Suitable dopants are mentioned below.

Further compounds suitable as hole transport material are for example mentioned in US2010/0219400, US2015/0073142 and US2015/0102331, e.g. the following compound

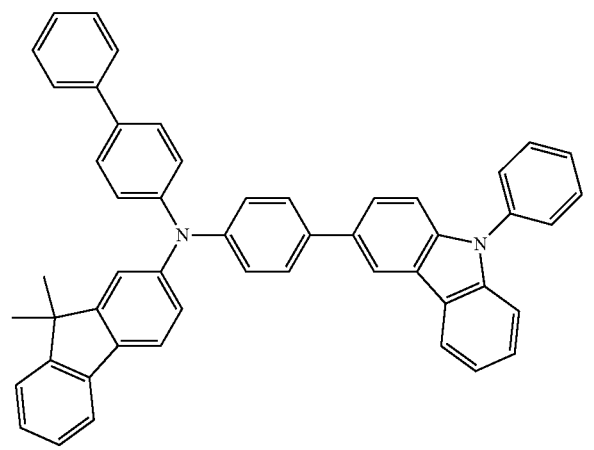 [SMILES: CC1(C)c2ccccc2-c2ccc(N(c3ccc(-c4ccccc4)cc3)c3ccc(-c4ccc5c(c4)c4ccccc4n5-c4ccccc4)cc3)cc21]

The compounds are employed in the hole transport layer in doped or undoped form. Suitable dopants are mentioned below.

Further compounds suitable as hole transport material are for example mentioned in US2008/0014464, e.g. the following compound

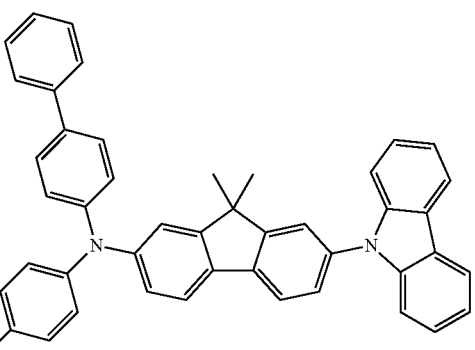

The compounds are employed in the hole transport layer in doped or undoped form. Suitable dopants are mentioned below.

Further compounds suitable as hole transport material are for example mentioned in WO2013/112557, e.g. the following compounds 1a to 12a mentioned in WO2013/112557:

-continued
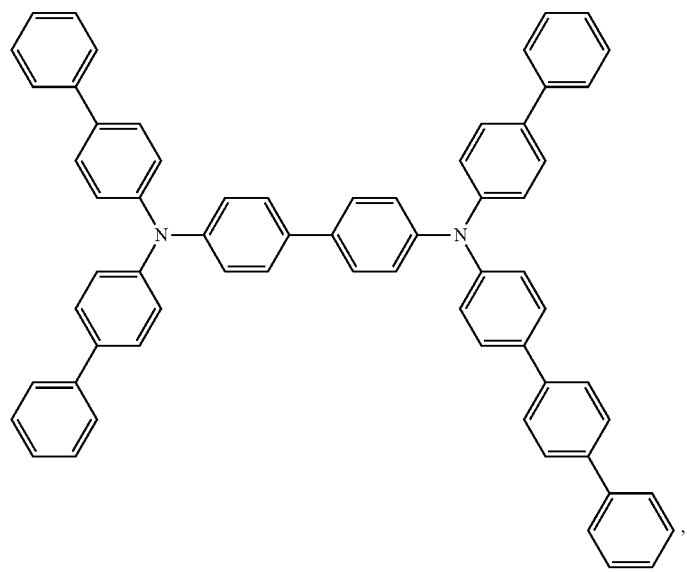
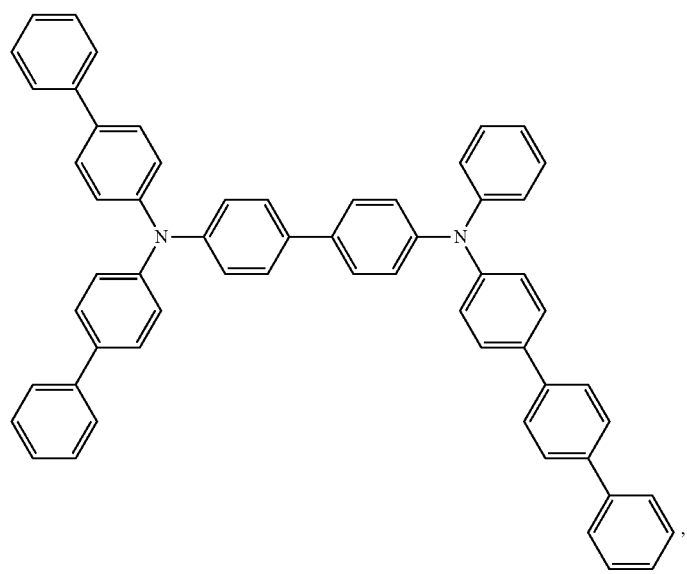
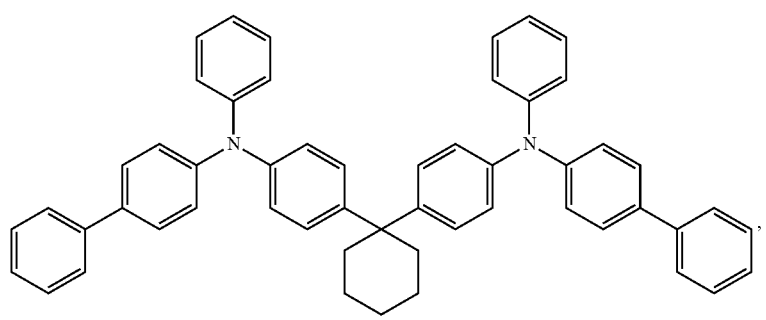

-continued
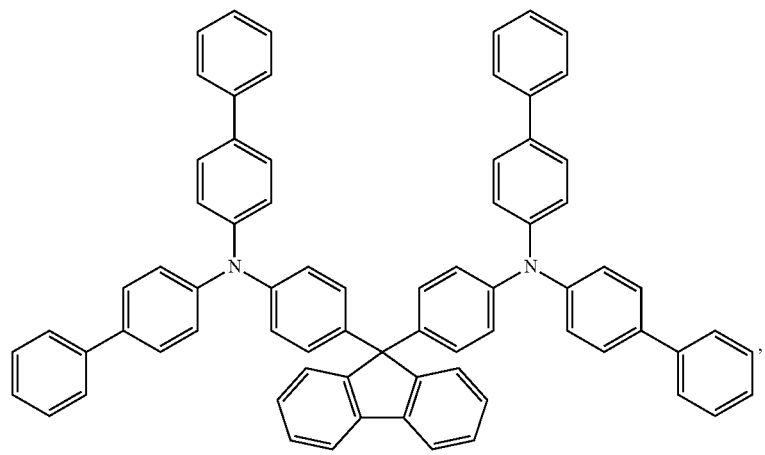
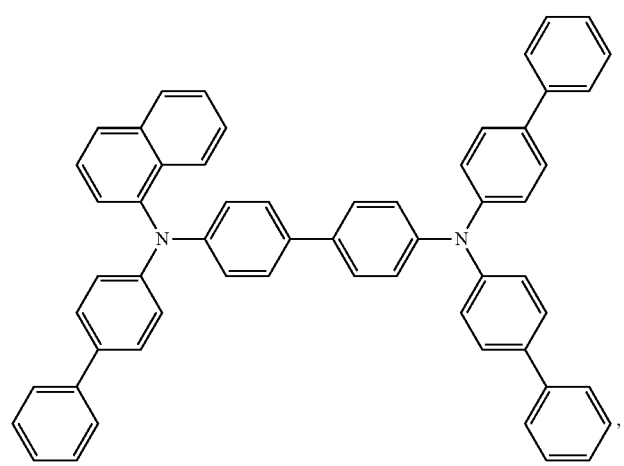
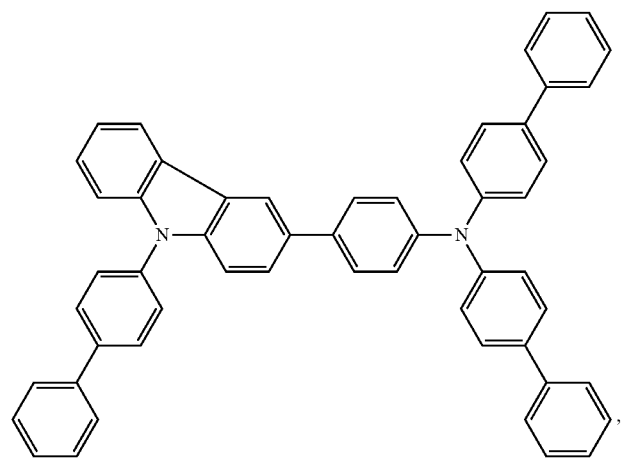

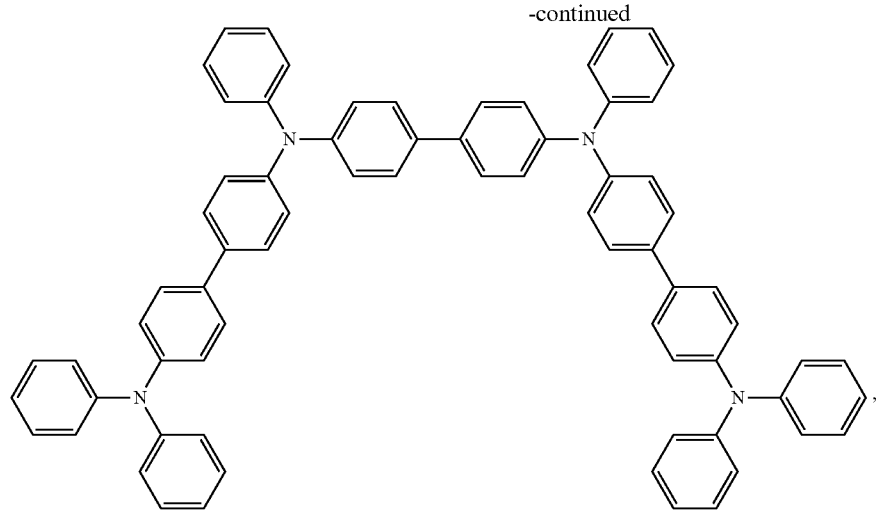
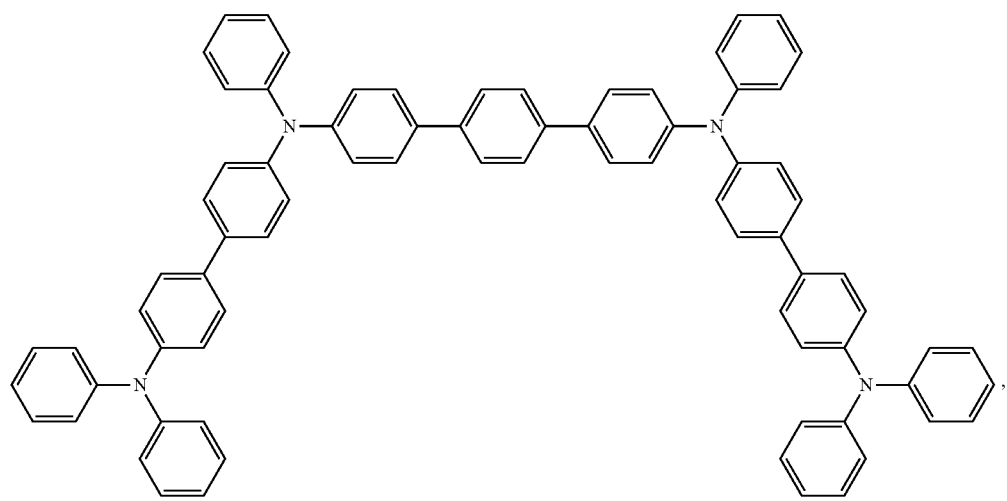
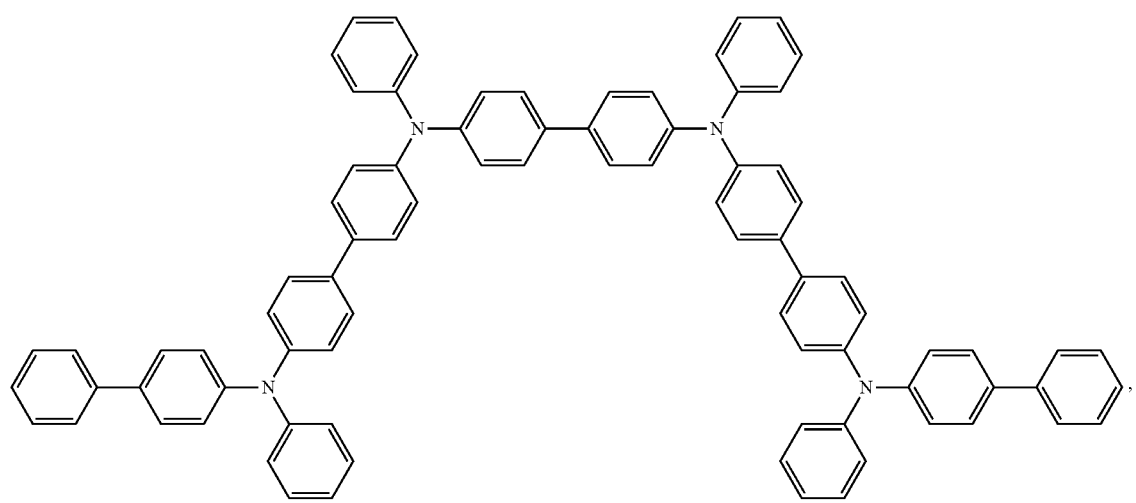

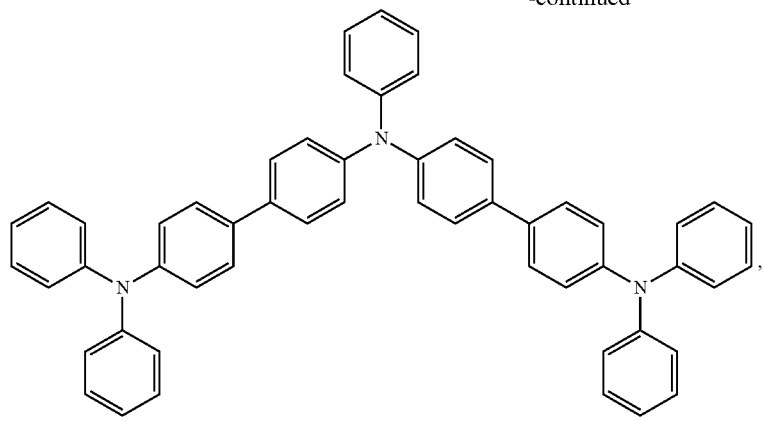

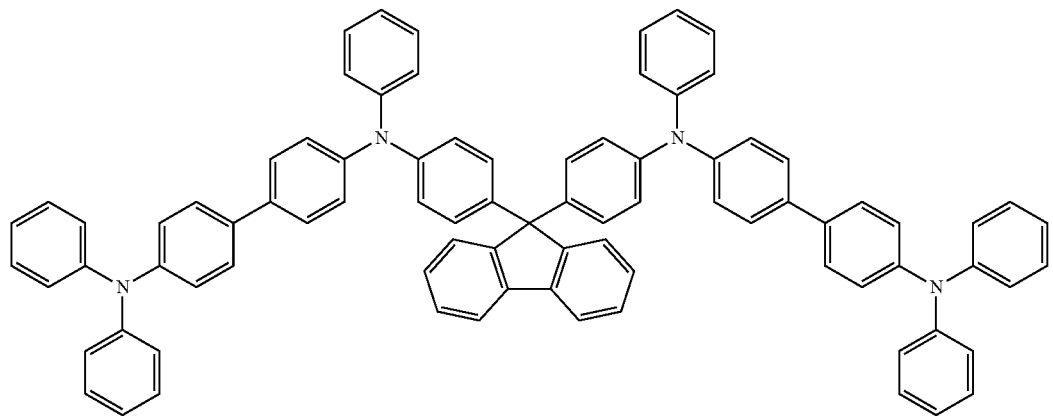

The hole-transporting layer may also be electronically doped in order to improve the transport properties of the materials used, in order firstly to make the layer thicknesses more generous (avoidance of pinholes/short circuits) and in order secondly to minimize the operating voltage of the device. Electronic doping is known to those skilled in the art and is disclosed, for example, in W. Gao, A. Kahn, J. Appl. Phys., Vol. 94, 2003, 359 (p-doped organic layers); A. G. Werner, F. Li, K. Harada, M. Pfeiffer, T. Fritz, K. Leo, Appl. Phys. Lett., Vol. 82, No. 25, 2003, 4495 and Pfeiffer et al., Organic Electronics 2003, 4, 89-103 and K. Walzer, B. Maennig, M. Pfeiffer, K. Leo, Chem. Soc. Rev. 2007, 107, 1233. For example it is possible to use mixtures in the hole-transporting layer, in particular mixtures which lead to electrical p-doping of the hole-transporting layer. p-Doping is achieved by the addition of oxidizing materials. These mixtures may, for example, be the following mixtures: mixtures of the abovementioned hole transport materials with at least one metal oxide, for example $MoO_2$, $MoO_3$, $WO_x$, $ReO_3$ and/or $V_2O_5$, preferably $MoO_3$ and/or $ReO_3$, more preferably $MoO_3$, or mixtures comprising the aforementioned hole transport materials and one or more compounds selected from 7,7,8,8-tetracyanoquinodimethane (TCNQ), 2,3,5,6-tetrafluoro-7,7,8,8-tetracyanoquinodimethane ($F_4$-TCNQ), 2,5-bis(2-hydroxyethoxy)-7,7,8,8-tetracyanoquinodimethane, bis(tetra-n-butylammonium)tetracyanodiphenoquinodimethane, 2,5-dimethyl-7,7,8,8-tetracyanoquinodimethane, tetracyanoethylene, 11,11,12,12-tetracyanonaphtho-2,6-quinodimethane, 2-fluoro-7,7,8,8-tetracyanoquino-dimethane, 2,5-difluoro-7,7,8,8-etracyanoquinodimethane, dicyanomethylene-1,3,4,5,7,8-hexafluoro-6H-naphthalen-2-ylidene)malononitrile ($F_6$-TNAP), Mo(tfd)$_3$ (from Kahn et al., J. Am. Chem. Soc. 2009, 131 (35), 12530-12531), compounds as described in EP1988587, US2008/265216, EP2180029, US2010/0102709, WO2010/132236, EP2180029 and quinone compounds as mentioned in EP2401254; as well as compounds as described in EP1713136 and WO2007/071450 and US2008/0265216.

Further materials useful in the hole transport layer are the following materials:

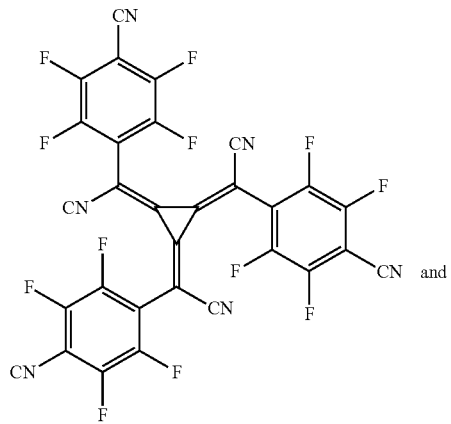

and

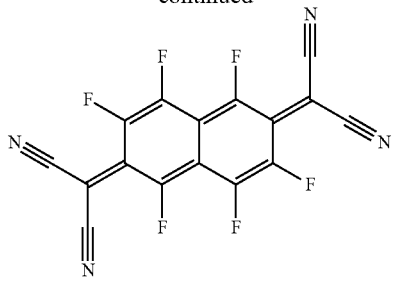

as well as NHT-49, NHT-51 (NHT-49, NHT-51 are commercially available from Novaled).

In addition to the hole transport materials mentioned above, the materials mentioned as hole injection materials in the hole injection layer are also useful as hole transport materials. Said materials may be used in undoped form or in combination with a p-dopant, for example in combination with $MoO_3$, F4-TCNQ or NDP-9, in the hole transport layer.

Electron/Exciton Blocking Layer (d)

Blocking layers may be used to reduce the number of charge carriers (electrons or holes) and/or excitons that leave the emissive layer. An electron/exciton blocking layer (d) may be disposed between the emitting layer (e) and the hole transport layer (c), to block electrons from emitting layer (e) in the direction of hole transport layer (c). Blocking layers may also be used to block excitons from diffusing out of the emissive layer. Suitable metal complexes for use as electron/exciton blocker material are, for example, carbene complexes as described in WO2005/019373A2, WO2006/056418A2, WO2007/115970, WO2007/115981, WO2008/000727, WO2012/121936A2, US2012/0305894A1, and WO2012/172482A1. Explicit reference is made here to the disclosure of the WO applications cited, and these disclosures shall be considered to be incorporated into the content of the present application. One example of a suitable carbene complex is compound HTM-1. Another example of a suitable carbene complex is compound HTM-2. The formulae of (HTM-1) and (HTM-2) are mentioned above.

Also suitable as electron/exciton blocker materials are the compounds mentioned in WO2012/130709; WO2013/050401; WO2014/009317; WO2014/044722; and the non-published European Patent Application EP13191100.0.

Further suitable electron/exciton blocker materials are the compounds of formula (H1) mentioned in WO2013/112557, as described above.

Further suitable electron/exciton blocker materials are the compounds mentioned in US2012/0223296.

Especially suitable are the compounds (H1-1), (H1-2), (H1-7) as mentioned above and the compounds (H1-3), (H1-4), (H1-5), (H1-6), (H1-8), (H1-9), (H1-10), (H1-11), (H1-12), (H1-13), (H1-14), (H1-15), (H-16) and (H1-17) as described in WO 2013/112557.

(Further suitable electron/exciton blocker materials are: NHT-49, NHT-51 (which are commercially available from Novaled) and HTM-211, Further compounds suitable as electron/exciton blocker materials are for example mentioned in US2010/0044689 and US2014/0217392, e.g. the following compound

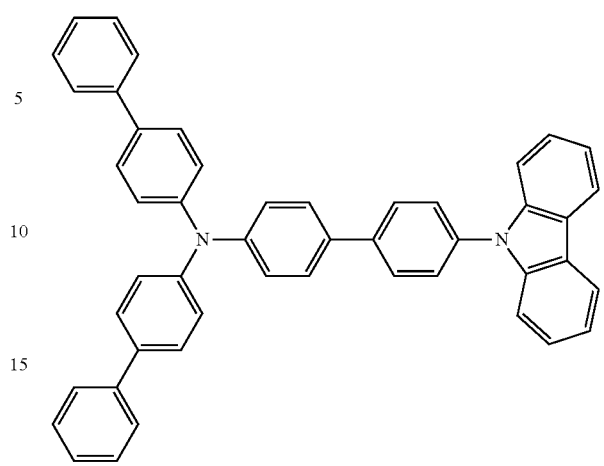

Further compounds suitable as electron/exciton blocker materials are for example mentioned in US2010/0219400, US2015/0073142 and US2015/0102331, e.g. the following compound

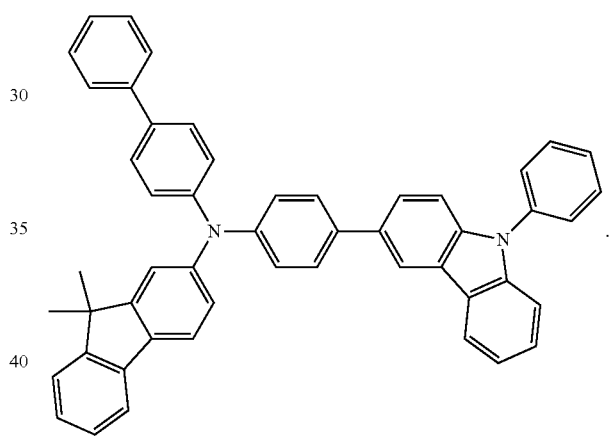

Further compounds suitable as electron/exciton blocker materials are for example mentioned in US2008/0014464, e.g. the following compound

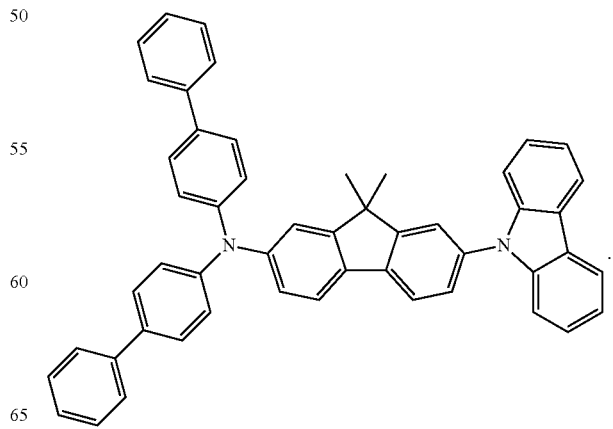

Hole/Exciton Blocking Layer (f)

Blocking layers may be used to reduce the number of charge carriers (electrons or holes) and/or excitons that leave the emissive layer. The hole blocking layer may be disposed between the emitting layer (e) and electron transport layer (g), to block holes from leaving layer (e) in the direction of electron transport layer (g). Blocking layers may also be used to block excitons from diffusing out of the emissive layer. Suitable hole/exciton blocking materials are, in principle, the host compounds mentioned above. The same preferences apply as for the host material.

Suitable hole/exciton blocker materials are therefore for example the materials containing both triphenylene and benzo-fused furans or benzo-fused thiophenes as mentioned above concerning suitable host materials.

Further hole/exciton blocking materials are one or more compounds of the general formula (X)

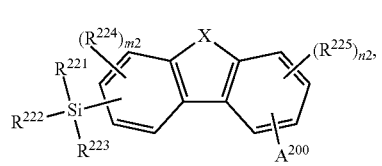

wherein

X is NR, S, O or PR;

R is aryl, heteroaryl, alkyl, cycloalkyl, or heterocycloalkyl;

$A^{200}$ is $-NR^{206}R^{207}$, $-P(O)R^{208}R^{209}$, $-PR^{210}R^{211}$, $-S(O)_2R^{212}$, $-S(O)R^{213}$, $-SR^{214}$, or $-OR^{215}$;

$R^{221}$, $R^{222}$ and $R^{223}$ are independently of each other aryl, heteroaryl, alkyl, cycloalkyl, or heterocycloalkyl, wherein at least one of the groups $R^{221}$, $R^{222}$, or $R^{223}$ is aryl, or heteroaryl;

$R^{224}$ and $R^{225}$ are independently of each other alkyl, cycloalkyl, heterocycloalkyl, aryl, heteroaryl, a group $A^{200}$, or a group having donor, or acceptor characteristics;

n2 and m2 are independently of each other 0, 1, 2, or 3;

$R^{206}$ and $R^{207}$ form together with the nitrogen atom a cyclic residue having 3 to 10 ring atoms, which can be unsubstituted, or which can be substituted with one, or more substituents selected from alkyl, cycloalkyl, heterocycloalkyl, aryl, heteroaryl and a group having donor, or acceptor characteristics; and/or which can be annulated with one, or more further cyclic residues having 3 to 10 ring atoms, wherein the annulated residues can be unsubstituted, or can be substituted with one, or more substituents selected from alkyl, cycloalkyl, heterocycloalkyl, aryl, heteroaryl and a group having donor, or acceptor characteristics; and $R^{208}$, $R^{209}$, $R^{210}$, $R^{211}$, $R^{212}$, $R^{213}$, $R^{214}$ and $R^{215}$ are independently of each other aryl, heteroaryl, alkyl, cycloalkyl, or heterocycloalkyl.

Compounds of formula (X) are described in WO2010/079051 (in particular pages on 19 to 26 and in tables on pages 27 to 34, pages 35 to 37 and pages 42 to 43).

Further suitable hole/exciton blocker materials are mentioned in US2013/0181190, especially in table 3, and US 2013/0119354, especially in table 4. Further suitable hole/exciton blocker materials are mentioned in US2014/0001446 and WO2015/014791.

Examples are bathocuprine compounds such as:

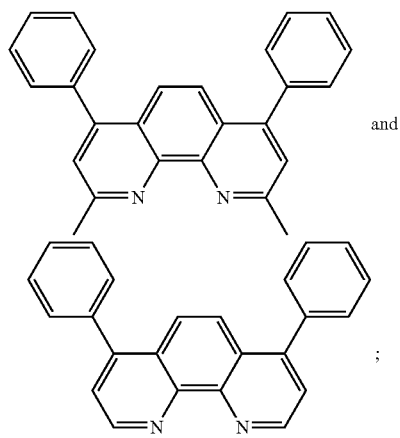

and

;

metal-8-hydroxy-quinolates such as:

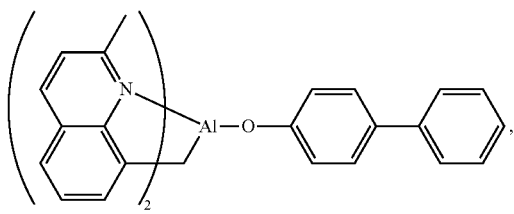

, triazoles, oxadiazoles, imidazoles, benzoimidazoles, triphenylene compounds, fluorinated aromatic compounds, phenothiazine-S-oxides, silylated five-membered nitrogen, oxygen, sulfur or phosphorous dibenzoheterocycles, or Aza-carbazoles.

Electron Transport Layer (g)

Electron transport layer may include a material capable of transporting electrons. Electron transport layer may be intrinsic (undoped), or doped. Doping may be used to enhance conductivity. Suitable electron-transporting materials for layer (g) of the inventive OLEDs comprise metals chelated with oxinoid compounds, such as tris(8-hydroxy-quinolato)aluminum ($Alq_3$), compounds based on phenanthroline such as 2,9-dimethyl-4,7-diphenyl-1,10phenanthroline (DDPA=BCP), 4,7-diphenyl-1,10-phenanthroline (Bphen), 2,4,7,9-tetraphenyl-1,10-phenanthroline, 4,7-diphenyl-1,10-phenanthroline (DPA) or phenanthroline derivatives disclosed in EP1786050, in EP1970371, or in EP1097981, and azole compounds such as 2-(4-biphenylyl)-5-(4-t-butylphenyl)-1,3,4-oxadiazole (PBD) and 3-(4-biphenylyl)-4-phenyl-5-(4-t-butylphenyl)-1,2,4-triazole (TAZ).

It is likewise possible to use mixtures of at least two materials in the electron-transporting layer, in which case at least one material is electron-conducting. Preferably, in such mixed electron-transporting layers, at least one phenanthroline compound is used, preferably BCP, or at least one pyridine compound according to the formula (VIII) below, preferably a compound of the formula (VIIIa) below. More preferably, in mixed electron-transporting layers, in addition to at least one phenanthroline compound, alkaline earth metal or alkali metal hydroxyquinolate complexes, for example Liq, are used. Suitable alkaline earth metal or alkali metal hydroxyquinolate complexes are specified below (formula VII). Reference is made to WO2011/157779.

The electron-transporting layer may also be electronically doped in order to improve the transport properties of the materials used, in order firstly to make the layer thicknesses more generous (avoidance of pinholes/short circuits) and in order secondly to minimize the operating voltage of the device. Electronic doping is known to those skilled in the art and is disclosed, for example, in W. Gao, A. Kahn, J. Appl. Phys., Vol. 94, No. 1, 1 Jul. 2003 (p-doped organic layers); A. G. Werner, F. Li, K. Harada, M. Pfeiffer, T. Fritz, K. Leo, Appl. Phys. Lett., Vol. 82, No. 25, 23 Jun. 2003 and Pfeiffer et al., Organic Electronics 2003, 4, 89-103 and K. Walzer, B. Maennig, M. Pfeiffer, K. Leo, Chem. Soc. Rev. 2007, 107, 1233. For example, it is possible to use mixtures which lead to electrical n-doping of the electron-transporting layer. n-Doping is achieved by the addition of reducing materials. These mixtures may, for example, be mixtures of the above-mentioned electron transport materials with alkali/alkaline earth metals or alkali/alkaline earth metal salts, for example Li, Cs, Ca, Sr, $Cs_2CO_3$, with alkali metal complexes, for example 8-hydroxyquinolatolithium (Liq), and with Y, Ce, Sm, Gd, Tb, Er, Tm, Yb, $Li_3N$, $Rb_2CO_3$, dipotassium phthalate, $W(hpp)_4$ from EP1786050, or with compounds described in EP1837926B1, EP1837927, EP2246862, WO2010132236 and DE102010004453.

In a preferred embodiment, the electron-transporting layer comprises at least one compound of the general formula (VII)

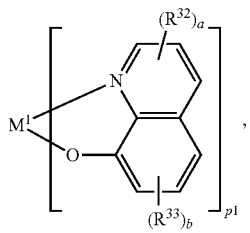

in which $R^{32}$ and $R^{33}$ are each independently F, $C_1$-$C_8$-alkyl, or $C_6$-$C_{14}$-aryl, which is optionally substituted by one or more $C_1$-$C_8$-alkyl groups, or two $R^{32}$ and/or $R^{33}$ substituents together form a fused benzene ring which is optionally substituted by one or more $C_1$-$C_8$-alkyl groups;

a and b are each independently 0, or 1, 2 or 3, $M^1$ is an alkaline metal atom or alkaline earth metal atom, p1 is 1 when $M^1$ is an alkali metal atom, p1 is 2 when $M^1$ is an earth alkali metal atom.

A very particularly preferred compound of the formula (VII) is

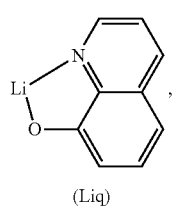

(Liq)

which may be present as a single species, or in other forms such as $Li_gQ_g$ in which g is an integer, for example $Li_6Q_6$. Q is an 8-hydroxyquinolate ligand or an 8-hydroxyquinolate derivative.

In a further preferred embodiment, the electron-transporting layer comprises at least one compound of the formula (VIII),

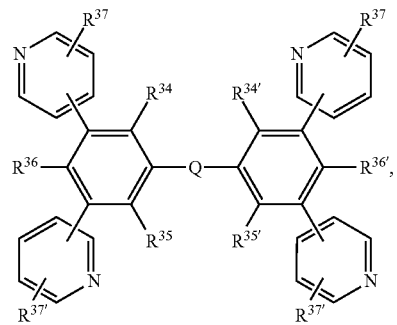

in which $R^{34}$, $R^{35}$, $R^{36}$, $R^{37}$, $R^{34'}$, $R^{35'}$, $R^{36'}$ and $R^{37'}$ are each independently H, $C_1$-$C_{18}$-alkyl, $C_1$-$C_{18}$-alkyl which is substituted by E and/or interrupted by D, $C_6$-$C_{24}$-aryl, $C_6$-$C_{24}$-aryl which is substituted by G, $C_2$-$C_{20}$-heteroaryl or $C_2$-$C_{20}$-heteroaryl which is substituted by G, Q is an arylene or heteroarylene group, each of which is optionally substituted by G;

D is —CO—; —COO—; —S—; —SO—; —$SO_2$—; —O—; —$NR^{40}$—; —$SiR^{45}R^{46}$—; —$POR^{47}$—; —$CR^{38}$=$CR^{39}$—; or —C≡C—;

E is —$OR^{44}$; —$SR^{44}$; —$NR^{40}R^{41}$; —$COR^{43}$; —$COOR^{42}$; —$CONR40R^{41}$; —CN; or F;

G is E, $C_1$-$C_{18}$-alkyl, $C_1$-$C_{18}$-alkyl which is interrupted by D, $C_1$-$C_{18}$-perfluoroalkyl, $C_1$-$C_{18}$-alkoxy, or $C_1$-$C_{18}$-alkoxy which is substituted by E and/or interrupted by D, in which $R^{38}$ and $R^{39}$ are each independently H, $C_6$-$C_{18}$-aryl; $C_6$-$C_{18}$-aryl which is substituted by $C_1$-$C_{18}$-alkyl or $C_1$-$C_{18}$-alkoxy; $C_1$-$C_{18}$-alkyl; or $C_1$-$C_{18}$-alkyl which is interrupted by —O—;

$R^{40}$ and $R^{41}$ are each independently $C_6$-$C_{18}$-aryl; $C_6$-$C_{18}$-aryl which is substituted by $C_1$-$C_{18}$-alkyl or $C_1$-$C_{18}$-alkoxy; $C_1$-$C_{18}$-alkyl; or $C_1$-$C_{18}$-alkyl which is interrupted by —O—; or $R^{40}$ and $R^{41}$ together form a 6-membered ring;

$R^{42}$ and $R^{43}$ are each independently $C_6$-$C_{18}$-aryl; $C_6$-$C_{18}$-aryl which is substituted by $C_1$-$C_{18}$-alkyl or $C_1$-$C_{18}$-alkoxy; $C_1$-$C_{18}$-alkyl; or $C_1$-$C_{18}$-alkyl which is interrupted by —O—, $R^{44}$ is $C_6$-$C_{18}$-aryl; $C_6$-$C_{18}$-aryl which is substituted by $C_1$-$C_{18}$-alkyl or $C_1$-$C_{18}$-alkoxy; $C_1$-$C_{18}$-alkyl; or $C_1$-$C_{18}$-alkyl which is interrupted by —O—, $R^{45}$ and $R^{46}$ are each independently $C_1$-$C_{18}$-alkyl, $C_6$-$C_{18}$-aryl or $C_6$-$C_{18}$-aryl which is substituted by $C_1$-$C_{18}$-alkyl, $R^{47}$ is $C_1$-$C_{18}$-alkyl, $C_6$-$C_{18}$-aryl or $C_6$-$C_{18}$-aryl which is substituted by $C_1$-$C_{18}$-alkyl.

Preferred compounds of the formula (VIII) are compounds of the formula (VIIIa)

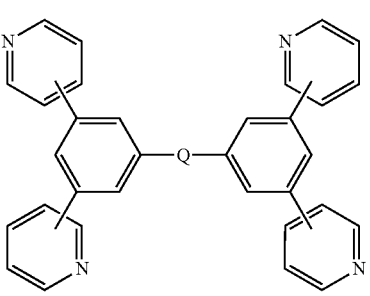

in which Q is:

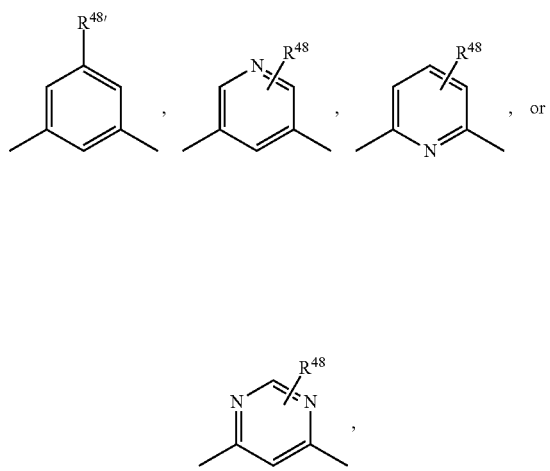

, or

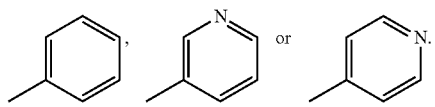

, $R^{48}$ is H or $C_1$-$C_{18}$-alkyl and
$R^{48'}$ is H, $C_1$-$C_{18}$-alkyl or

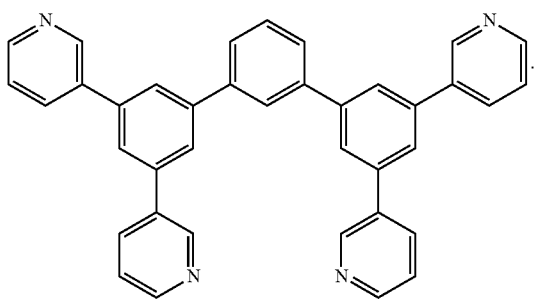

Particular preference is given to a compound of the formula (ETM-2)

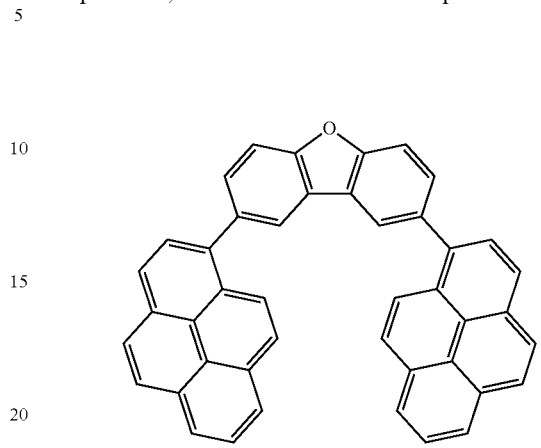

In a further, very particularly preferred embodiment, the electron-transporting layer comprises a compound Liq and a compound ETM-2.

In a preferred embodiment, the electron-transporting layer comprises the compound of the formula (VII) in an amount of 99 to 1% by weight, preferably 75 to 25% by weight, more preferably about 50% by weight, where the amount of the compounds of the formulae (VII) and the amount of the compounds of the formulae (VIII) adds up to a total of 100% by weight.

The preparation of the compounds of the formula (VIII) is described in J. Kido et al., Chem. Commun. (2008) 5821-5823, J. Kido et al., Chem. Mater. 20 (2008) 5951-5953 and JP2008/127326, or the compounds can be prepared analogously to the processes disclosed in the aforementioned documents.

It is likewise possible to use mixtures of alkali metal hydroxyquinolate complexes, preferably Liq, and dibenzofuran compounds in the electron-transporting layer. Reference is made to WO2011/157790. Dibenzofuran compounds A-1 to A-36 and B-1 to B-22 described in WO2011/157790 are preferred, wherein dibenzofuran compound

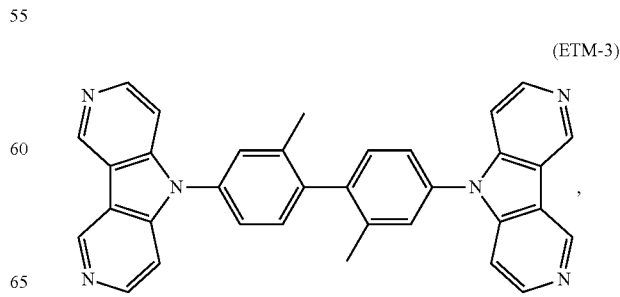

(A-10; = ETM-1)

is most preferred.

In a preferred embodiment, the electron-transporting layer comprises Liq in an amount of 99 to 1% by weight, preferably 75 to 25% by weight, more preferably about 50% by weight, where the amount of Liq and the amount of the dibenzofuran compound(s), especially ETM-1, adds up to a total of 100% by weight.

In a preferred embodiment, the electron-transporting layer comprises at least one phenanthroline derivative and/or pyridine derivative.

In a further preferred embodiment, the electron-transporting layer comprises at least one phenanthroline derivative and/or pyridine derivative and at least one alkali metal hydroxyquinolate complex.

In a further preferred embodiment, the electron-transporting layer comprises at least one of the dibenzofuran compounds A-1 to A-36 and B-1 to B-22 described in WO2011/157790, especially ETM-1.

In a further preferred embodiment, the electron-transporting layer comprises a compound described in WO2012/111462, WO2012/147397, WO2012/014621, such as, for example, a compound of formula (ETM-3)

US2012/0261654, such as, for example, a compound of formula (ETM-4)

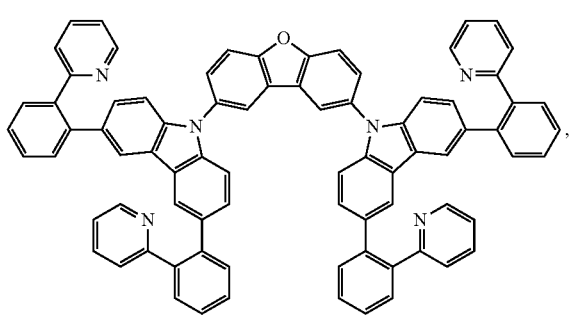

and WO2012/115034, such as for example, such as, for example, a compound of formula (ETM-5)

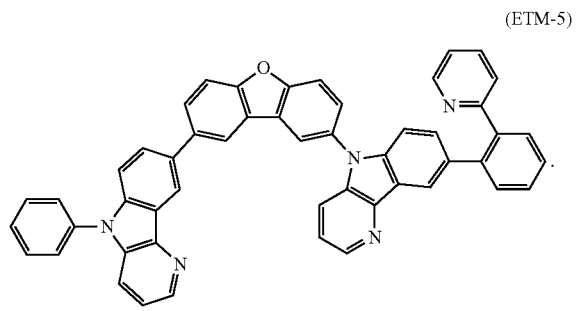 [SMILES: c1ccc(-n2c3ccc(-c4ccc5oc6ccc(-n7c8ccc(-c9ccccc9-c9ccccn9)cc8c8ncccc87)cc6c5c4)cc3c3ncccc32)cc1]

Further suitable electron transport materials are mentioned in US2013/0181190, especially in table 3, and US2013/0119354, especially in table 4.

Further suitable electron transport materials are mentioned in WO2013/079678, especially the compounds mentioned in the examples.

Further suitable electron transport materials are mentioned in EP2452946, especially compound (28) on page 5 and compound (10) on page 6.

A further suitable electron transport material is

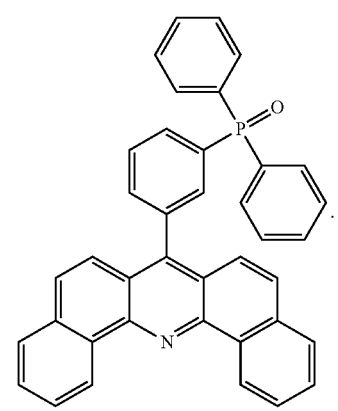 [SMILES: O=P(c1ccccc1)(c1ccccc1)c1cccc(-c2c3ccc4ccccc4c3nc3c2ccc2ccccc23)c1]

Further suitable electron transport materials are mentioned in EP2434559 and WO2013/187896, for example:

As n-dopant, for example the material mentioned in EP 1 837 926 is employed.

Electron Injection Layer (h)

The electron injection layer may be any layer that improves the injection of electrons into an adjacent organic layer. Lithium-comprising organometallic compounds such as 8-hydroxyquinolatolithium (Liq), CsF, NaF, KF, $Cs_2CO_3$ or LiF may be applied between the electron transport layer (g) and the cathode (i) as an electron injection layer (h) in order to reduce the operating voltage.

Cathode (i)

The cathode (i) is an electrode which serves to introduce electrons or negative charge carriers. The cathode may be any metal or nonmetal which has a lower work function than the anode. Suitable materials for the cathode are selected from the group consisting of alkali metals of group 1, for example Li, Cs, alkaline earth metals of group 2, metals of group 12 of the Periodic Table of the Elements, comprising the rare earth metals and the lanthanides and actinides. In addition, metals such as aluminum, indium, calcium, barium, samarium and magnesium, and combinations thereof, may be used.

In general, the different layers in the inventive OLED, if present, have the following thicknesses:

anode (a): 12 to 500 nm, preferably 40 to 500, more preferably 50 to 500 nm, most preferably 100 to 200 nm; in a further most preferred embodiment: 40 to 120 nm;

hole injection layer (b): 1 to 100 nm, preferably 5 to 100 nm, more preferably 2 to 80 nm, most preferably 20 to 80 nm, hole-transport layer (c): 5 to 200 nm, preferably 5 to 100 nm, more preferably 10 to 80 nm;

electron/exciton blocking layer (d): 1 to 50 nm, preferably 5 to 10 nm, preferably 3 to 10 nm;

light-emitting layer (e): 1 to 100 nm, preferably 5 to 60 nm, preferably 5 to-40 nm;

hole/exciton blocking layer (f): 1 to 50 nm, preferably 5 to 10 nm, preferably 3 to 10 nm;

electron-transport layer (g): 5 to 100 nm, preferably 20 to 80 nm; preferably 20 to 50 nm;

electron injection layer (h): 1 to 50 nm, preferably 2 to 10 nm;

cathode (i): 20 to 1000 nm, preferably 30 to 500 nm.

The inventive OLED can be produced by methods known to those skilled in the art. In general, the OLED is produced by successive vapor deposition of the individual layers onto a suitable substrate. Suitable substrates are, for example, glass, inorganic materials such as ITO or IZO or polymer films. For the vapor deposition, customary techniques may be used, such as thermal evaporation, chemical vapor deposition (CVD), physical vapor deposition (PVD) and others. In case of an active matrix OLED display (AMOLED), the substrate can be an AMOLED backplane.

In an alternative process, the organic layers may be coated from solutions or dispersions in suitable solvents, in which case coating techniques known to those skilled in the art are employed. Suitable coating techniques are, for example, spin-coating, the casting method, the Langmuir-Blodgett ("LB") method, the inkjet printing method, dip-coating, letterpress printing, screen printing, doctor blade printing, slit-coating, roller printing, reverse roller printing, offset lithography printing, flexographic printing, web printing, spray coating, coating by a brush or pad printing, and the like. Among the processes mentioned, in addition to the aforementioned vapor deposition, preference is given to spin-coating, the inkjet printing method and the casting method since they are particularly simple and inexpensive to perform. In the case that layers of the OLED are obtained by the spin-coating method, the casting method or the inkjet printing method, the coating can be obtained using a solution prepared by dissolving the composition in a concentration of 0.0001 to 90% by weight in a suitable organic solvent such as benzene, toluene, xylene, tetrahydrofuran, methyltetrahydrofuran, N,N-dimethylformamide, acetone, acetonitrile, anisole, dichloromethane, dimethyl sulfoxide, water and mixtures thereof.

It is possible that the layers of the OLED are all produced by the same coating method. Furthermore, it is likewise possible to conduct two or more different coating methods to produce the layers of the OLED.

The inventive OLEDs can be used in all devices in which electroluminescence is useful. Suitable devices are preferably selected from stationary and mobile visual display units and illumination means. Further suitable devices are devices such as keyboards; items of clothing; furniture; and wallpaper. The present invention therefore also relates to a device selected from the group consisting of stationary visual display units; mobile visual display units; illumination means; keyboards; items of clothing; furniture; and wallpaper comprising an inventive OLED or an inventive light-emitting layer.

Stationary visual display units are, for example, visual display units of computers, televisions, visual display units in printers, kitchen appliances and advertising panels, illuminations and information panels. Mobile visual display units are, for example, visual display units in cellphones, laptops, tablet PCs, digital cameras, mp-3 players, smartphones, vehicles, and destination displays on buses and trains.

The inventive metal complexes can additionally be used in OLEDs with inverse structure. In these inverse OLEDs, the inventive complexes are in turn preferably used in the light-emitting layer. The structure of inverse OLEDs and the materials typically used therein are known to those skilled in the art.

The present invention further provides a white OLED comprising at least one inventive metal complex. In a preferred embodiment, the inventive metal complex is used as emitter material in the white OLED. Preferred embodiments of the inventive metal complexes have been specified above. Suitable structures of white OLEDs and suitable components are known by a person skilled in the art.

In order to obtain white light, the OLED must generate light which colors the entire visible range of the spectrum. However, organic emitters normally emit only in a limited portion of the visible spectrum—i.e. are colored. White light can be generated by the combination of different emitters. Typically, red, green and blue emitters are combined. However, the prior art also discloses other methods for formation of white OLEDs, for example the triplet harvesting approach. Suitable structures for white OLEDs or methods for formation of white OLEDs are known to those skilled in the art.

In one embodiment of a white OLED, several dyes are layered one on top of another in the light-emitting layer of an OLED and hence combined (layered device). This can be achieved by mixing all dyes or by direct series connection of different-colored layers. The expression "layered OLED" and suitable embodiments are known to those skilled in the art.

In a further embodiment of a white OLED, several different-colored OLEDs are stacked one on top of another (stacked device). For the stacking of two OLEDs, what is called a charge generation layer (CG layer) is used. This CG layer may be formed, for example, from one electrically n-doped and one electrically p-doped transport layer. The expression "stacked OLED" and suitable embodiments are known to those skilled in the art.

In further embodiments of this "stacked device concept", it is also possible to stack only two or three OLEDs or to stack more than three OLEDs.

In a further embodiment of white OLEDs, the two concepts mentioned for white light generation can also be combined. For example, a single-color OLED (for example blue) can be stacked with a multicolor layered OLED (for example red-green). Further combinations of the two concepts are conceivable and known to those skilled in the art.

The inventive metal complex can be used in any of the layers mentioned above in white OLEDs. In a preferred embodiment, it is used in one or more or all light-emitting layer(s) of the OLED(s), in which case the structure of the invention metal complex is varied as a function of the use of the complex. Suitable and preferred components for the further layers of the light OLED(s) or materials suitable as matrix material in the light-emitting layer(s) and preferred matrix materials are likewise specified above.

EXAMPLES

The examples which follow, more particularly the methods, materials, conditions, process parameters, apparatus and the like detailed in the examples, are intended to support the present invention, but not to restrict the scope of the present invention. All experiments are carried out in protective gas atmosphere.

Example 1

Complex (A-1)

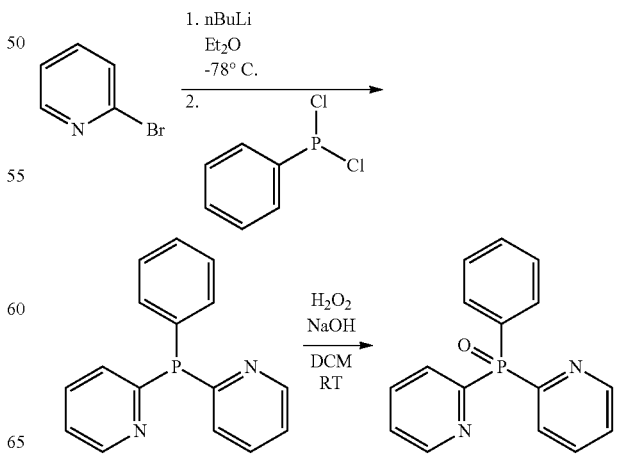

a) Bis(2-pyridyl)phenylphosphine oxide.

2-Bromopyridine (2 eq, 0.15 mol, 24.1 g, 14.5 ml) was dissolved in diethyl ether (480 ml) under argon. The solution was cooled to −70° C. n-Butyllithium (2.1 eq, 0.16 mol, 100 ml, 1.6 M) was added dropwise over 60 min. The temperature did not exceed −65° C. It was stirred at −70° C. for additional 35 min. In a second flask, dichlorophenylphosphine (1 eq, 0.076 mol, 13.6 g, 10.3 ml) was dissolved in diethyl ether (160 ml) and the solution was cooled to −78° C. The solution of the lithiated pyridine was added to the dichlorophenylphosphine solution via cannula. Stirring at −78° C. was continued for one hour, then, the reaction mixture was brought to room temperature by stirring over night. The reaction mixture was poured into water (200 ml). After stirring for some minutes the layers were separated and the aqueous layer was extracted with DCM (2×100 ml). The combined organic layers were washed with brine (100 ml) and were dried over MgSO$_4$. The solvent was removed in vacuo. The crude phosphine intermediate was dissolved in DCM (200 ml) and 0.5 M aqueous NaOH (100 ml) was added, followed by 33% aqueous hydrogen peroxide solution (40 ml). The mixture was vigorously stirred at room temperature for 45 min, after which the TLC showed no more phosphine intermediate. The layers were separated and the organic layer was washed with water (100 ml), sat. NaHSO$_3$ solution (100 ml), again water (100 ml) and finally brine (100 ml). It was dried over MgSO$_4$ and the solvent was removed in vacuo. The crude product was recrystallized from toluene. Bis(2-pyridyl)-phenylphosphine oxide was obtained as beige powder (11.9 g, 0.043 mmol, 66%).

$^1$H-NMR (400 MHz, CDCl$_3$): δ=8.79 (d, 2H, pyH-6, $^3$J=4.5 Hz), 8.14-8.09 (m, 4H), 7.83-7.78 (m, 2H, pyH), 7.57-7.53 (m, 1H, pPh), 7.50-7.46 (m, 2H), 7.40-7.36 (m, 2H, pyH-3).

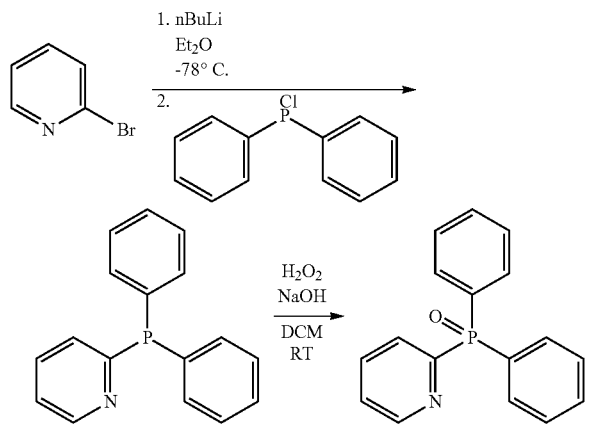

b) (2-Pyridyl)bisphenylphosphine oxide.

The compound was synthesized in analogy to bis(2-pyridyl)¬phenyl¬phosphine oxide by using 2-bromopyridine (1 eq, 0.063 mol, 10.0 g, 6.0 ml) in diethyl ether (200 ml), nBuLi (1.05 eq, 0.066 mol, 42 ml, 1.6 M), chlorodiphenylphosphine (1 eq, 0.063 mol, 14.0 g, 11.7 ml) in diethyl ether (150 ml) under argon. The final product was purified by recrystallization from toluene. (2-Pyridyl)bisphenylphosphine oxide was obtained as beige powder (9.12 g, 0.033 mmol, 52%).

$^1$H-NMR (400 MHz, CDCl$_3$): δ=8.78 (d, 1H, pyH-6, $^3$J=4.5 Hz), 8.33-8.30 (m, 1H), 7.91-7.84 (m, 5H), 7.55-7.50 (m, 2H, pPh), 7.47-7.43 (m, 4H), 7.41-7.37 (m, 1H, pyH-3).

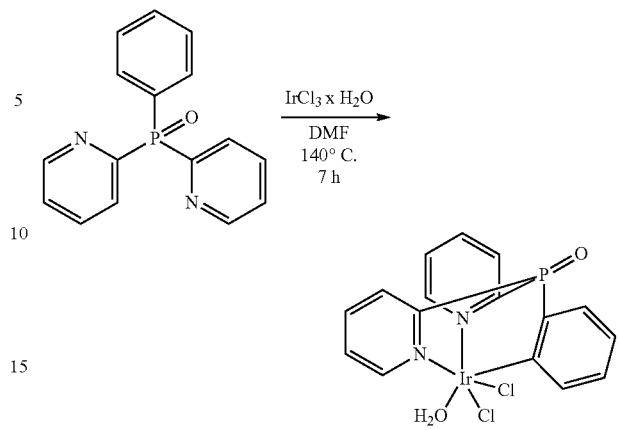

c) (Bis(2-pyridyl)phenylphosphine oxide)iridium dichloride.

Bis(2-pyridyl)phenylphosphine oxide (1 eq, 1.78 mmol, 500 mg) and IrCl$_3$xH$_2$O (1 eq, 1.78 mmol, 646 mg) were dissolved in DMF (100 ml) under argon. The solution was degassed and subsequently heated to 140° C. for 7 h. After cooling to room temperature, the solvent was removed in vacuo. The residue was suspended in DCM using the ultrasonic bath. Hexane was added for precipitation of the product. The solids were filtered off, washed with hexane, little water, little ethanol, diethyl ether and again hexane. (Bis(2-pyridyl)phenylphosphine oxide)iridium dichloride (637 mg, 1.10 mmol, 62%) was obtained as yellow-green powder after drying in vacuo. A mixture of two isomers was obtained.

TLC: Rf=0.27+0.17, silica, DCM/MeOH (10:1)

$^1$H-NMR (400 MHz, CDCl$_3$): δ=9.59 [9.17] (d, 2H, $^3$J=6 Hz), 8.17-8.15 [8.07-8.05] (m, 4H), 7.91-7.88 [7.76-7.73] (m, 1H), 7.68-7.52 (m, 3H), 7.08-7.01 (m, 2H) MALDI (neg. mode): m/z=541 [M−H$_2$O—H]$^-$ After recrystallization from a DCM/methanol mixture, one isomer was obtained.

$^1$H-NMR (400 MHz, DMF-d7): δ=9.17 (d, 2H, $^3$J=6 Hz), 8.31-8.23 (m, 4H), 8.00-7.96 (m, 1H), 7.76-7.67 (m, 3H), 7.13-7.06 (m, 2H)

$^1$H-NMR (400 MHz, CD$_2$Cl$_2$/CD$_3$OD): δ=9.42 (d, 2H, $^3$J=6 Hz, pyH), 8.23 (t, 2H, pyH), 8.10 (t, 2H, pyH), 7.88-7.84 (m, 1H, PhH), 7.77-7.72 (m, 1H, PhH), 7.59-7.55 (m, 1H, pyH), 7.19-7.09 (m, 2H, PhH)

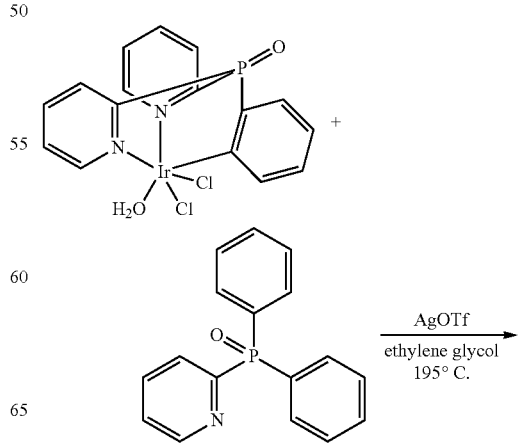

-continued

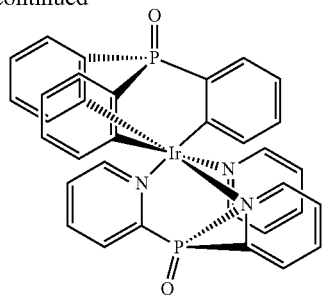

d) (Bis(2-pyridyl)phenylphosphine oxide)iridium(III) (2-pyridyl)bisphenylphosphine oxide.

(2-Pyridyl)bisphenylphosphine oxide (3 eq, 0.26 mmol, 73 mg) and AgOTf (2 eq, 0.17 mmol, 45 mg) were dissolved in ethylene glycol (7 ml) under argon and the solution was degasssed and subsequently heated up to 140° C. (Bis(2-pyridyl)phenylphosphine oxide)iridium dichloride (1 eq, 0.087 mmol, 50 mg) was added and it was further heated up to 195° C. for 15 h. After cooling to room temperature the reaction mixture was poured into water (50 ml) and DCM (25 ml). The layers were separated and the aqueous layer was extracted with DCM (2×25 ml). The combined organic layers were washed with water (50 ml) and brine (50 ml) and it was dried over $MgSO_4$. The solvent was removed in vacuo and the resiude was purified via silica column chromatography with DCM/ethyl acetate/ethanol (8:2:0.5). Complex (A-1) was isolated from the green luminescent fractions (~1 mg).

TLC: Rf=0.12, silica, DCM/EE/EtOH (8:2:1.5)

$^1$H-NMR (400 MHz, $CD_2Cl_2$): δ=8.57-8.51 (m, 3H), 8.04-8.01 (m, 2H), 7.97-7.90 (m, 4H), 7.28-7.27 (m, 2H), 7.09-6.64 (m, 7H), 6.79-6.75 (m, 1H), 6.71-6.68 (m, 2H), 6.23-6.20 (m, 1H), 5.94-5.92 (m, 2H).

HPLC-HRMS (pos. mode): m/z=750.1033 [M+H]$^+$, calc. [M+H]$^+$ m/z=750.1051

Photophysical Properties of Complex (A-1)

The photoluminescent properties of complex (A-1) were measured in a 1% PMMA film.

Table 1 shows the data in comparison to the PL properties of green emitter Ir(ppy)$_3$. A very high photoluminescence quantum yield (PLQY) of 100% was measured, which is higher than the PLQY of the reference emitter Ir(ppy)$_3$.

The triplet decay showed a monoexponential fit and a decay time of around 2.2 μs. The full-width-half-maximum (FWHM) of the emission band is small and the emission spectrum shows a Gaussian shaped profile comparable to Ir(ppy)$_3$ (see FIG. 2). The emission color of complex (A-1) is blue-shifted compared to green emitter Ir(ppy)$_3$.

The invention claimed is:
1. A metal complex of formula $L^1ML^2$ (I), wherein
M is selected from Ir and Rh,
$L^1$ is a ligand of formula

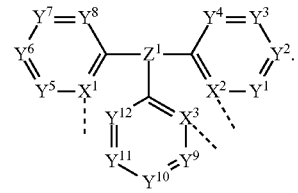

(IIa), $L^2$ is a ligand of formula

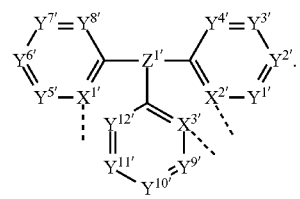

(IIb), wherein
$Z^1$ and $Z^{1'}$ are Si—$R^4$,
$X^1$, $X^2$, $X^3$, $X^{1'}$, $X^{2'}$ and $X^{3'}$ are independently of each other N, or C,
$R^4$ are independently of each other a $C_1$-$C_{18}$ alkyl group, which can optionally be substituted by at least one substituent E and/or interrupted by D; a $C_6$-$C_{14}$ aryl group, which can optionally be substituted by at least one substituent G; a heteroaryl group comprising 3 to 11 ring atoms, which can optionally be substituted by at least one substituent G, a $C_3$-$C_{12}$ cycloalkyl group, which can optionally be substituted by at least one substituent E; or a $C_1$-$C_{18}$ alkoxy group,
$Y^1$, $Y^2$, $Y^3$, $Y^4$, $Y^5$, $Y^6$, $Y^7$, $Y^8$, $Y^9$, $Y^{10}$, $Y^{11}$, $Y^{12}$, $Y^{1'}$, $Y^{2'}$, $Y^{3'}$, $Y^{4'}$, $Y^{5'}$, $Y^{6'}$, $Y^{7'}$, $Y^{8'}$, $Y^{9'}$, $Y^{10'}$, $Y^{11'}$ and $Y^{12'}$ are independently of each other $CR^6$, or N,
$R^6$ is independently in each occurrence H, a halogen atom; $NO_2$; a $C_1$-$C_{18}$ haloalkyl group; CN; $C_1$-$C_{18}$ alkyl group, which can optionally be substituted by at least one substituent E and/or interrupted by D; a $C_6$-$C_{14}$ aryl group, which can optionally be substituted by at least one substituent G; a heteroaryl group comprising 3 to 11 ring atoms, which can optionally be substituted by at least one substituent G; a —O—$C_6$-$C_{14}$ aryl group, which can optionally be substituted by at least one substituent G; a $C_3$-$C_{12}$ cycloalkyl group, which can optionally be substituted by at least one substituent E; or a $C_1$-$C_{18}$ alkoxy group, $NR^7R^8$ or $SiR^{80}R^{81}R^{82}$;

TABLE 1

| PMMA Film | Ext. [nm] | Em. [nm] | PLQY [%] | $T_v$ [μs]$^a$ | $T_0$ [μs]$^b$ | CIE-x | CIE-y | FWHM [nm] | FWHM [eV] |
|---|---|---|---|---|---|---|---|---|---|
| 2% Ir[ppy]$_3$ | 370 | 530 | 90 | 1.69 | 1.87 | 0.318 | 0.621 | 76 | 0.331 |
| 1% Complex (A-1) | 400 | 499 | 100 | 2.17 | 2.17 | 0.229 | 0.514 | 77 | 0.368 |

$^a T_v = (a_1T_1 + a_2T_2)/(a_1 + a_2)$;
$^b T_0 = T_v/QY$

R[7] and R[8] are independently of each other H, an unsubstituted $C_6$-$C_{18}$ aryl group; a $C_6$-$C_{18}$ aryl group which is substituted by $C_1$-$C_{18}$ alkyl, $C_1$-$C_{18}$ alkoxy; or a $C_1$-$C_{18}$ alkyl group, which can optionally be interrupted by —O—;

D is —S—, $NR^{65}$, or —O—;

E is —$OR^{69}$, $CF_3$, $C_1$-$C_8$ alkyl or F;

G is —$OR^{69}$, $CF_3$ or $C_1$-$C_8$ alkyl;

$R^{65}$ is a phenyl group, which can optionally be substituted by one or two $C_1$-$C_8$ alkyl groups; an unsubstituted $C_1$-$C_{18}$ alkyl group; or a $C_1$-$C_{18}$ alkyl group, which is interrupted by —O—;

$R^{69}$ is a phenyl group, which can optionally be substituted by one or two $C_1$-$C_8$ alkyl groups; an unsubstituted $C_1$-$C_{18}$ alkyl group; or a $C_1$-$C_{18}$ alkyl group, which is interrupted by —O—, $R^{80}$, $R^{81}$ and $R^{82}$ are independently of each other a $C_1$-$C_{25}$ alkyl group, which can optionally be interrupted by O; a $C_6$-$C_{14}$ aryl group, which can optionally be substituted by $C_1$-$C_{18}$ alkyl; or a heteroaryl group comprising 3 to 11 ring atoms, which can optionally be substituted by $C_1$-$C_{18}$ alkyl, and ╌ is the bonding site to M, with the proviso that three of $X^1$, $X^2$, $X^3$, $X^{1'}$, $X^{2'}$ and $X^{3'}$ are C.

2. The metal complex according to claim 1, wherein
$X^1$, $X^2$ and $X^{1'}$ are N,
$X^3$, $X^{2'}$ and $X^{3'}$ are C.

3. The metal complex according to claim 1, wherein M is Ir.

4. The metal complex according to claim 1, wherein $Y^1$, $Y^2$, $Y^3$, $Y^4$, $Y^5$, $Y^6$, $Y^7$, $Y^8$, $Y^9$, $Y^{10}$, $Y^{11}$, $Y^{12}$, $Y^{1'}$, $Y^{2'}$, $Y^{3'}$, $Y^{4'}$, $Y^{5'}$, $Y^{6'}$, $Y^{7'}$, $Y^{8'}$, $Y^{9'}$, $Y^{10'}$, $Y^{11'}$ and $Y^{12'}$ are independently of each other $CR^6$, wherein $R^6$ is defined in claim 1.

5. The metal complex according to claim 4, wherein $R^6$ is independently in each occurrence H, F, Cl, $NO_2$; $CF_3$; CN; a $C_1$-$C_{18}$ alkyl group, a $C_1$-$C_{18}$ alkoxy group, a phenyl group, a phenoxy group, or $NR^7R^8$, R[7] and R[8] are independently of each other H, or a $C_1$-$C_{18}$ alkyl group, which can optionally be interrupted by —O—.

6. The metal complex according to claim 1, wherein $Z^1$ and $Z^{1'}$ are Si—$R^4$, wherein $R^4$ are independently of each other a $C_1$-$C_{18}$ alkyl group, a phenyl group, which is optionally substituted by a $C_1$-$C_8$ alkyl group; or a $C_1$-$C_{18}$ alkoxy group.

7. An organic electronic device, comprising at least one metal complex according to claim 1.

8. The organic electronic device according to claim 7, wherein the organic electronic device is selected from organic light-emitting diodes (OLEDs), organic photovoltaic cells (OPVs), organic field-effect transistors (OFETs) and light-emitting electrochemical cells (LEECs).

9. An apparatus selected from the group consisting of stationary visual display units, mobile visual display units, illumination units, keyboards, items of clothing, furniture, and wallpaper comprising the organic electronic device according to claim 7.

10. A light-emitting layer comprising at least one metal complex according to claim 1.

11. The light-emitting layer according to claim 10, comprising at least one metal complex of formula (I) and at least one host material.

12. A device selected from the group consisting of electrophotographic photoreceptors, photoelectric converters, organic solar cells (organic photovoltaics), switching elements, organic light emitting field effect transistors (OLEFETs), image sensors, dye lasers and electroluminescent devices and as emitter, matrix material, charge transport material and charge or exciton blocker, comprising a metal complex according to claim 1.

13. A metal complex of formula

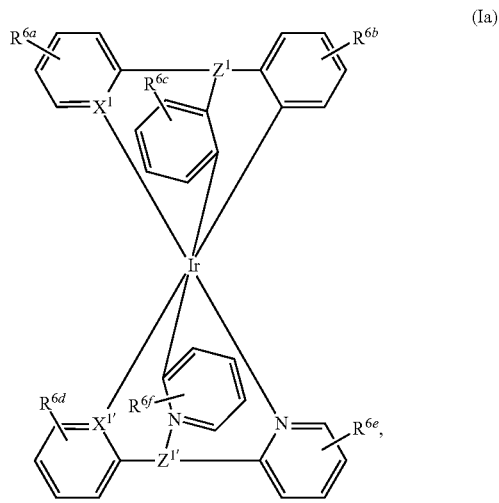

wherein
$X^1$ and $X^{1'}$ are C, or N,
$R^{6a}$, $R^{6b}$, $R^{6c}$, $R^{6d}$, $R^{6e}$ and $R^{6f}$ are independently of each other H, F, Cl, $NO_2$; $CF_3$; CN; a $C_1$-$C_{18}$ alkyl group, a $C_1$-$C_{18}$ alkoxy group, a phenyl group, a phenoxy group, or $NR^7R^8$, R[7] and R[8] are independently of each other H, or a $C_1$-$C_{18}$ alkyl group, which can optionally be interrupted by —O—, and
$Z^1$ is Si—$R^4$ and $Z^{1'}$ is N, P=O, or Si—$R^4$, wherein $R^4$ are independently of each other a $C_1$-$C_{18}$ alkyl group, a phenyl group, which is optionally substituted by a $C_1$-$C_8$ alkyl group; or a $C_1$-$C_{18}$ alkoxy group.

14. An organic electronic device, comprising at least one metal complex according to claim 13.

15. The organic electronic device according to claim 14, wherein the organic electronic device is selected from organic light-emitting diodes (OLEDs), organic photovoltaic cells (OPVs), organic field-effect transistors (OFETs) and light-emitting electrochemical cells (LEECs).

16. An apparatus selected from the group consisting of stationary visual display units, mobile visual display units, illumination units, keyboards, items of clothing, furniture, and wallpaper comprising the organic electronic device according to claim 14.

17. A light-emitting layer comprising at least one metal complex according to claim 13.

18. The light-emitting layer according to claim 17, comprising at least one metal complex of formula (Ia), and at least one host material.

19. A device selected from the group consisting of electrophotographic photoreceptors, photoelectric converters, organic solar cells (organic photovoltaics), switching elements, organic light emitting field effect transistors (OLEFETs), image sensors, dye lasers and electroluminescent devices and as emitter, matrix material, charge transport material and charge or exciton blocker, comprising a metal complex according to claim 13.

20. A process for the preparation of the metal complex of formula $L^1ML^2$ (I), comprising reacting a metal complex of formula $L^1MX_3$ with a compound of formula

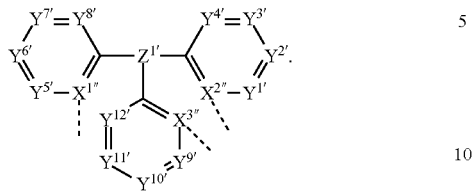

in a solvent in the presence of an auxiliary agent and optionally a base at elevated temperature, wherein
X is Cl, Br, $C_1$-$C_8$ alkyl-OH, N,N-dimethylformamide, dimethyl sulfoxide, tetrahydrofuran, or $H_2O$,
$X^{1''}$, $X^{2''}$ and $X^{3''}$ are CH, or N,
M, $L^1$, $L^2$, $Z^{1'}$, $Y^{1'}$, $Y^{2'}$, $Y^{3'}$, $Y^{4'}$, $Y^{5'}$, $Y^{6'}$, $Y^{7'}$, $Y^{8'}$, $Y^{9'}$, $Y^{10'}$, $Y^{11'}$ and $Y^{12'}$ are defined in claim 1,
with the proviso that at least one of $X^{1''}$, $X^{2''}$ and $X^{3''}$ is CH.

* * * * *